(12) United States Patent
Palmese et al.

(10) Patent No.: US 11,629,220 B2
(45) Date of Patent: Apr. 18, 2023

(54) RENEWABLE FURAN BASED AMINE CURING AGENTS FOR EPOXY THERMOSET

(71) Applicants: DREXEL UNIVERSITY, Philadelphia, PA (US); The Government of the United States of America, as represented by The Secretary of the Army, Washington, DC (US)

(72) Inventors: Giuseppe R. Palmese, Hainesport, NJ (US); Santosh K. Yadav, Geneva, OH (US); John Vergara, Downingtown, PA (US); John J. LaScala, Wilmington, DE (US)

(73) Assignees: Drexel Unversity, Philadelphia, PA (US); The Government of the United States of America, as represented by The Secretary of the Army, Washington, DC (US)

(*) Notice: Subject to any disclaimer, the term of this patent is extended or adjusted under 35 U.S.C. 154(b) by 33 days.

(21) Appl. No.: 16/640,155

(22) PCT Filed: Aug. 21, 2018

(86) PCT No.: PCT/US2018/047135
§ 371 (c)(1),
(2) Date: Feb. 19, 2020

(87) PCT Pub. No.: WO2019/040389
PCT Pub. Date: Feb. 28, 2019

(65) Prior Publication Data
US 2020/0172658 A1    Jun. 4, 2020

Related U.S. Application Data

(60) Provisional application No. 62/547,949, filed on Aug. 21, 2017.

(51) Int. Cl.
*C08G 59/50* (2006.01)
*C07D 307/52* (2006.01)
(Continued)

(52) U.S. Cl.
CPC ....... *C08G 59/5046* (2013.01); *C07D 307/52* (2013.01); *C07D 407/06* (2013.01);
(Continued)

(58) Field of Classification Search
None
See application file for complete search history.

(56) References Cited

U.S. PATENT DOCUMENTS 4,496,751 A * 1/1985 Still ..................... C07D 307/52
528/73
2017/0009005 A1* 1/2017 Urban .................. C08G 59/184

FOREIGN PATENT DOCUMENTS

CN        100487021 C    5/2009
WO    WO-9302071 A1 *  2/1993  ........... C07D 307/52
(Continued)

OTHER PUBLICATIONS

Skouta et al., "New method for the synthesis of Difuranic Diamines and Teterafuranic Tetra-Amines," Synthetic Communications, 24 (18), pp. 2571-2576 (1994) (Year: 1994).*
(Continued)

*Primary Examiner* — Randy P Gulakowski
*Assistant Examiner* — Ha S Nguyen
(74) *Attorney, Agent, or Firm* — Mendelsohn Dunleavy, P.C.

(57) ABSTRACT

The present invention relates novel furan based amine cross-linkers with improved thermomechanical and water barrier properties. The novelty of this invention is the use of aromatic, and hydrophobic aliphatic aldehydes to bridge two furfuryl amines, which yields a diamine or tetra amines with
(Continued)

a significantly enhanced hydrophobic character. These diamine cross-linkers exhibit enhanced water barrier properties and thermomechanical properties when cured with both commercial and synthetic epoxies.

1 Claim, 10 Drawing Sheets

(51) Int. Cl.
    C07D 407/06    (2006.01)
    C07D 407/14    (2006.01)
    C08G 59/24    (2006.01)
    C08G 59/32    (2006.01)
    C08G 18/32    (2006.01)
    C08G 18/73    (2006.01)
    C08G 18/75    (2006.01)
    C08G 18/76    (2006.01)
    C08G 18/77    (2006.01)
    C08G 69/26    (2006.01)
(52) U.S. Cl.
    CPC ......... *C07D 407/14* (2013.01); *C08G 59/245* (2013.01); *C08G 59/3236* (2013.01)

(56) References Cited

FOREIGN PATENT DOCUMENTS

| WO | WO9302071 A1 | 2/1993 | | |
|---|---|---|---|---|
| WO | WO-9302072 A1 | * | 2/1993 | ........... C07D 307/52 |
| WO | WO199302072 A1 | | 2/1993 | |
| WO | WO-2015124792 A1 | * | 8/2015 | ........... C08G 59/223 |

OTHER PUBLICATIONS

Auvergne, Rémi, et al. "Biobased Thermosetting Epoxy: Present and Future." Chemical Reviews 114.2 (2013): 1082-1115.
Baroncini, Elyse A., et al. "Recent advances in bio-based epoxy resins and bio-based epoxy curing agents." Journal of Applied Polymer Science 133.45 (2016): 44103 (19 pages).
Beaman, R. G., et al. "Interfacial Polycondensation. III. Polyamides." Journal of Polymer Science 40.137 (1959): 329-336.
Froidevaux, Vincent, et al. "Biobased Amines: From Synthesis to Polymers; Present and Future." Chemical Reviews 116.22(2016): 14181-14224.
Gandini, Alessandro, et al. "Progress of Polymers from Renewable Resources: Furans, Vegetable Oils, and Polysaccharides." Chemical Reviews 116.3 (2016): 1637-1669.
Higashi, Fukuji, and Yuji Taguchi. "Effects of the Rates of Initiation and Propagation on a Direct Polycondensation Reaction with Triphenyl Phosphite and Pyridine." Journal of Polymer Science: Polymer Chemistry Edition 19.12 (1981): 3345-3349.
Higashi, Fukuji, et al. "Effect of Initiation Conditions on the Direct Polycondensation Reaction Using Triphenyl Phosphite and Pyridine." Journal of Polymer Science: Polymer Chemistry Edition 19.11 (1981): 2745-2750.
Higashi, Fukuji, and Nobuyuki Kokubo. "Synthesis of Polyhydrazides and Poly (amide-Hydrazide)s by the Direct Polycondensation Reaction with Triphenyl Phosphite and LiCl." Journal of Polymer Science: Polymer Chemistry Edition 18.5 (1980): 1639-1642.
Holfinger, Michael S., et al. "Synthesis of Difurfuryl Diamines by the Acidic Condensation of Furfurylamine with Aldehydes and Their Mechanism of Formation." The Journal of Organic Chemistry 60.6 (1995): 1595-1598.
Hu, Fengshuo, et al. "Synthesis and Characterization of Thermosetting Furan-Based Epoxy Systems." Macromolecules 47.10 (2014): 3332-3342.
Hu, Fengshuo, et al. "Preparation and Characterization of Fully Furan-Based Renewable Thermosetting Epoxy-Amine Systems." Macromolecular Chemistry and Physics 216.13 (2015): 1441-1446.
Kishimoto, Akira. "Diffusion of Vapours in Organic Coatings." Progress in Organic Coatings 1.2 (1972): 91-112.
Morgan, Paul W., and Stephanie L. Kwolek. "Interfacial Polycondensation. XII. Variables Affecting Stirred Polycondensation Reactions." Journal of Polymer Science 62.173 (1962): 33-58.
Morgan, Paul W., and Stephanie L. Kwolek. "Interfacial Polycondensation. II. Fundamentals of Polymer Formation at Liquid Interfaces." Journal of Polymer Science 40.137 (1959): 299-327.
Shen, Xiaobin, et al. "Synthesis of high performance polybenzoxazine networks from bio-based furfurylamine: Furan vs benzene ring." Polymer 122 (2017): 258-269.
Van der Wel, G. K. et al., "Moisture in organic coatings—a review." Progress in Organic Coatings 37.1-2 (1999): 1-14.
Vanlandingham, M. R., et al. "Moisture Diffusion in Epoxy Systems." Journal of Applied Polymer Science 71.5 (1999): 787-798.
Vergara, J., et al. "583-Synthesis, characterization, and water uptake studies of renewable fully furan based epoxy/amine thermosetting materials." PMSE: Division of Polymeric Materials Science and Engineering. Abstract Only.
Wittbecker, Emerson L., and Paul W. Morgan. "Interfacial Polycondensation. I." Journal of Polymer Science 40.137 (1959): 289-297.
Peterson, Amy et al., "Thermoreversible and remendable glass-polymer interface for fiber-reinforced composites." Composites Science and Technology 71.5 (2011): 586-592.
International Search Report and Written Opinion for corresponding International application No. PCT/US2018/047135; dated Dec. 21, 2018; (17 pages).
Abid, Souhir, et al. "A preliminary study of polyureas and poly(parabanic acid)s incorporating furan rings." Polymer Bulletin 57.1 (2006): 43-50.
Skouta, M., et al. "New Method for the Synthesis of Difuranic Diamines and Tetrafuranic Tetra-Amines." Synthetic Communications 24.18 (1994): 2571-2576.
Gharbi, S. et al., "Synthesis of entirely new furanic polyamides", Journal de la Société Chimique de Tunisie, 6.1 (2004): 17-25 (Machine Translation).
Crank, J., "The Mathematics of Diffusion", 2nd Edition Book, Oxford University Press: 1975.
La Scala, John et al., "Environmentally Friendly High Performance Bio-Based Composites for DoD Applications", Poster, ASETSDefense 2016 Poster Presentations, Dec. 6, 2016.
Extended European Search Report for corresponding European application No. PCT/US2018047135; dated Nov. 17, 2020 (9 pages).
Maktouf, Leila Ben, et al. "Polyimides based on furanic diamines and aromatic dianhydrides: synthesis, characterization and properties." Polymer Bulletin 67.7 (2011): 1111-1122.

\* cited by examiner

RENEWABLE FURAN BASED AMINE CURING AGENTS FOR EPOXY THERMOSET

CROSS REFERENCE TO RELATED APPLICATIONS

This application claims the benefit of U.S. Provisional Application No. 62/547,949, filed on Aug. 21, 2017, the entire disclosure of which is hereby incorporated by reference as if set forth fully herein.

STATEMENT OF GOVERNMENT INTEREST

This invention was made with government support under Contract Number W911NF-15-2-0017 awarded by the United States Army Research Laboratory. The Government has certain rights in the invention.

FIELD OF THE INVENTION

The present invention relates to novel furan based amine cross-linkers with improved thermomechanical and water barrier properties.

BRIEF DESCRIPTION OF THE STATE OF THE ART

Recently, biobased epoxy system educed from renewable resources have been increasingly important as sustainable and eco-friendly products which have the ability to replace the products based on petroleum feedstocks.[1-3] Thermoset network systems obtained from renewable resources have attracted enormous attention from industry, as well as academic research. Thus far, several types of bio-based resources have been investigated to obtain bio-based epoxy systems including, for example, vegetable oils, cellulose, hemicellulose, lignin, starch, and chitin.[4]

Comprising about 40 to 50 wt % of the entire thermoset, amine hardeners also significantly impact the ultimate performance of thermosetting epoxy/amine materials.[4-5] Therefore, it is necessary to take amine hardeners into account when designing renewable alternatives. Aromatic amine hardeners are commonly utilized since they endow cured thermosets with superior thermomechanical properties. However, most of these hardeners, such as 4,4'-methylenedianiline (MDA) and diethyltoluenediamine (DETDA) with phenyl building blocks, are non-renewable and toxic.[4]

Several building blocks are derived from cellulose, mainly furanyl has unique chemistry and characteristics. The furanyl building blocks display a variety of features that are associated with the structure and properties of the heterocycle.[6] Renewable furanyl derivatives are reported as promising candidates for preparing thermosetting epoxy/amine materials due to their feasibility, aromaticity and eco-friendliness.[3] Several furanyl amine hardeners have been reported in literature, however thermosets made with these furanyl based curing agents have poor properties, particularly a poor glass transition temperature and poor water barrier properties. Furan based epoxy curing agents are needed which significantly improve the thermomechanical and water barrier properties.

The present invention relates to various furan based di- and tetra-amines made using acidic condensation of aldehydes with furfuryl amine.[5,7] The epoxy thermosets made with these amines showed superior thermomechanical and water barrier properties when cured with diglycidyl ether of bisphenol A (DGEBA).

F. Hu et al., *Macromolecules,* 2014 relates to furan-based epoxy/amine thermosetting materials. Furfurylamine is reacted with formaldehyde or acetaldehyde to produce difuran diamines. The specific difuran diamines disclosed in F. Hu et al. are 5, 5'-methylenedifurfurylamine and 5,5'-ethylidenedifurfurylamine.

WO 93/02071 discloses methods for preparing difuran diammonium salts for the manufacture of isocyanates, from which polyurethanes are obtained. The method comprises mixing furfurylamine with HX acid to cause protonation of the amine and placing the product in the presence of a carbonyl compound, in an acidic medium to produce DADF (Diammonium difuran). The diamine difurans of WO 93/02071 have the general formula:

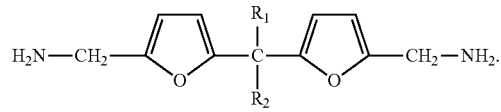

In a first embodiment, $R_1$ and $R_2$, are identical or different, and are either an aryl radical or an alkyl radical having a carbon chain having between 3 and 6 carbons. In another embodiment, $R_1$ is either hydrogen, a methyl or an ethyl radical, and $R_2$ is either an aryl radical or an alkyl radical having a carbon chain having between 3 and 6 carbons.

U.S. Pat. No. 4,496,751 relates to difuran diamine compounds as an alternative to oil-derived isocyanates. This patent generally discloses the formula:

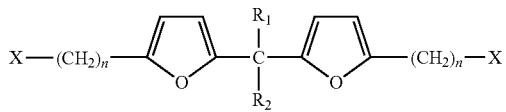

wherein $R_1$ and $R_2$ are the same or different and are selected from the group consisting of hydrogen, unsubstituted ethyl radicals, methyl radicals, vinyl radicals, halogen substituted vinyl radicals, halogen substituted methyl radicals and halogen substituted ethyl radicals, X is a $-NH_2$ or $-NCO$ group, and n is 0 or 1 with the proviso that n is not 0 when X is $-NH_2$.

SUMMARY OF THE INVENTION

The present invention relates to difuran diamine compounds, epoxy thermosets made from the difuran diamine compounds as curing agents, polymers comprising the epoxy thermoset therein, and methods of preparing each of the foregoing.

The following sentences describe some embodiments of the invention.

1. In a first aspect, the disclosure relates to a compound selected from compounds of the following Formulae (I) and (II):

(A) a difuran diamines of the Formula (I),

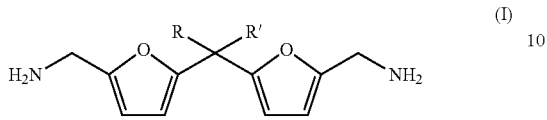

(I)

wherein (i) R may be hydrogen and $R^1$ may be selected from an optionally substituted alkyl group having 4 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; the alkyl group, the alkene group, the cycloalkyl group, the aryl group and the heterocyclic group of $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms, and when $R^1$ is a phenyl group, the phenyl group must be substituted; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms; or (iii) R may be selected from hydrogen, an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; the alkyl group, the alkene group, the cycloalkyl group, the aryl group and the heterocyclic group of R may be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ may be a phenyl group of the following structure:

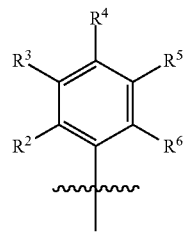

wherein

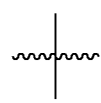

represents the attachment point to the methylene carbon bridging the furan rings in Formula (I); $R^2$, $R^3$, $R^4$, $R^5$, and $R^6$ may be independently selected from hydrogen, a hydroxyl group, an alkoxy group having 1 to 20 carbon atoms, an optionally substituted alkyl group having 1 to 20 carbon atoms, an optionally substituted alkene group having 2 to 20 carbon atoms, an optionally substituted aryl group having 6 to 10 carbon atoms, an optionally substituted heterocyclic group having 3 to 9 carbon atoms, and an optionally substituted cycloalkyl group having 3 to 12 carbon atoms; the alkyl group, the alkene group, the aryl group, the heterocyclic group, and the cycloalkyl group of $R^2$, $R^3$, $R^4$, $R^5$, and $R^6$ may be substituted with 1 to 5 substituents independently selected from halogen, hydroxy, amino, nitro, cyano, carboxy, an alkyl group having 1 to 20 carbons, an alkoxy group, and a heterocyclic group having 1 to 20 carbon atoms; and when R is hydrogen, at least one of $R^2$, $R^3$, $R^4$, $R^5$ and $R^6$ may not be hydrogen; and B) a tetrafuran tetraamine of the Formula (II),

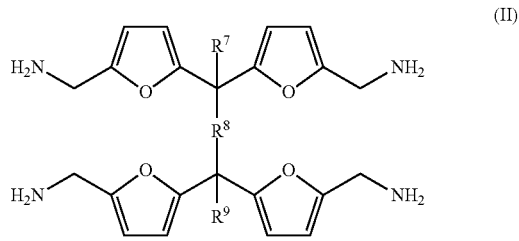

(II)

wherein $R^7$ and $R^9$ may be independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group of $R^7$ and $R^9$ can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and the aryl group substituent and the heterocyclic group substituent may be further substituted with hydroxy, an alkoxy group having 1 to 20 carbon atoms, or an alkylamino group having 1 to 2 carbon atoms; and $R^8$ may be an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; the alkylene group, the alkenylene group, the divalent heterocyclic group, the arylene group, and the cycloalkylene group of $R^8$ may be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

2. The compound of sentence 1, wherein R and $R^1$ may be independently selected from hydrogen, an optionally substituted alkyl group having 7 to 20 carbon atoms, an optionally substituted alkene group having 3 to 20 carbon atoms, an optionally substituted cycloalkyl group having 3 to 12 carbon atoms and a phenyl group of the following structure:

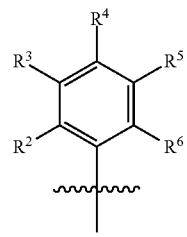

and the alkyl group, the alkene group, and the cycloalkyl group of R and $R^1$ may be substituted with 1 to 5 substituents independently selected from a heterocyclic group having 3 to 16 carbons, a hydroxyl group, and an alkoxy group having 1 to 20 carbon atoms;

represents the attachment point to the methylene carbon bridging the furan rings in the Formula (I); $R^2$, $R^3$, $R^4$, $R^5$, and $R^6$ may be independently selected from hydrogen, a hydroxyl group, an alkoxy group having 1 to 20 carbon atoms, an optionally substituted alkyl group having 1 to 20 carbon atoms, an optionally substituted alkene group having 2 to 20 carbon atoms, an optionally substituted aryl group having 6 to 10 carbon atoms, an optionally substituted heterocyclic group having 3 to 9 carbon atoms, and an optionally substituted cycloalkyl group having 3 to 12 carbon atoms; the alkyl group, the alkene group, the aryl group, the heterocyclic group, and the cycloalkyl group of $R^2$, $R^3$, $R^4$, $R^5$, and $R^6$ may be substituted with 1 to 5 substituents independently selected from a hydroxyl group, an alkoxy group, and a heterocyclic group having 1 to 20 carbon atoms; wherein at least one of $R^2$, $R^3$, $R^4$, $R^5$ and $R^6$ may not be a hydrogen when one of R and $R^1$ is hydrogen, and wherein only one of R and $R^1$ may be hydrogen.

3. The compound of sentence 1, wherein R may be hydrogen, and $R^1$ may be selected from a phenyl group of the following structure:

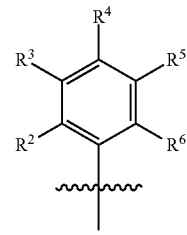

wherein

represents the attachment point to the methylene carbon bridging the furan rings in Formula (I); $R^2$, $R^3$, $R^4$, $R^5$, and $R^6$ are independently selected from hydrogen, a hydroxyl group, an alkoxy group having 1 to 4 carbon atoms, an alkyl group having 1 to 6 carbon atoms, and an alkene group having 2 to 4 carbon atoms; and at least one of $R^2$, $R^3$, $R^4$, $R^5$ and $R^6$ is not hydrogen.

4. The compound of sentence 1, wherein R and $R^1$ may each be independently selected from hydrogen, an optionally substituted alkyl group having 8 to 18 carbon atoms, an optionally substituted alkene group having 4 to 18 carbon atoms, and an optionally substituted cycloalkyl group having 3 to 8 carbon atoms, the alkyl group, the alkene group, and the cycloalkyl group of R and $R^1$ may be substituted with 1 to 5 substituents independently selected from halogen, hydroxy, amino, nitro, cyano, carboxy, an alkyl group having 1 to 8 carbons, and an alkoxy group having 1 to 8 carbon atoms; and only one of R and $R^1$ can be hydrogen.

5. The compound of sentence 1, wherein the furan containing compound may be the tetrafuran tetraamine compound of Formula (II):

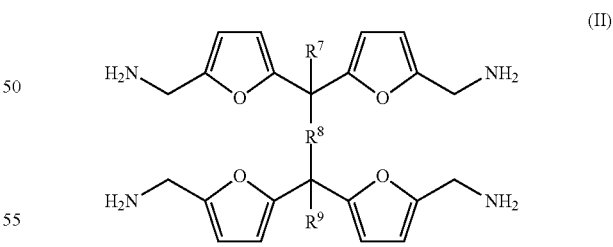

wherein $R^7$ and $R^9$ may be independently selected from hydrogen, an optionally substituted alkyl group having 1 to 18 carbon atoms, an optionally substituted alkene group having 2 to 18 carbon atoms, an optionally substituted heterocyclic group with 3 to 8 carbon atoms, an optionally substituted aryl group having 6 to 9 carbon atoms and an optionally substituted cycloalkyl group having 3 to 12 carbon atoms; and the alkyl group, the alkene group, the heterocyclic group, the aryl group, and the cycloalkyl group of $R^7$ and $R^9$ may be substituted with 1 to 5 substituents independently selected from halogen, hydroxy, amino, nitro, cyano, carboxy, an alkyl group having 1 to 8 carbons, an alkoxy group having 1 to 8 carbon atoms, and a heterocyclic group having 3 to 10 carbon atoms; and $R^8$ may be selected from an optionally substituted alkylene group having 1 to 18 carbon atoms, an optionally substituted alkenylene group having 2 to 18 carbon atoms, an optionally substituted divalent heterocyclic group with 3 to 8 carbon atoms, and an optionally substituted arylene group having 6 to 9 carbon atoms and an optionally substituted cycloalkylene group having 3 to 12 carbon atoms; and the alkylene group, the alkenylene group, the divalent heterocyclic group, the arylene group, and the cycloalkylene group of $R^8$ may be substituted with 1 to 4 substituents independently selected from halogen, hydroxy, amino, nitro, cyano, carboxy, an alkyl group having 1 to 8 carbons, an alkoxy group having 1 to 8 carbon atoms, and a heterocyclic group having 3 to 10 carbon atoms.

6. The compound of sentence 1, wherein the furan containing compound may be the tetrafuran tetraamine compound of Formula (II):

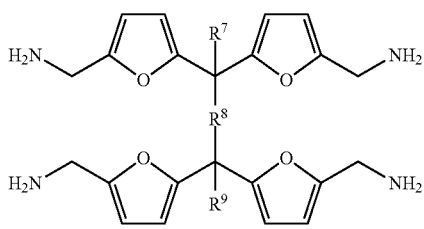

(II)

wherein $R^7$ and $R^9$ may be independently selected from hydrogen, an optionally substituted alkyl group having 1 to 8 carbon atoms, an optionally substituted alkene group having 2 to 8 carbon atoms, an optionally substituted heterocyclic group with 3 to 6 carbon atoms, an optionally substituted aryl group having 6 to 9 carbon atoms and an optionally substituted cycloalkyl group having 3 to 8 carbon atoms; and the alkyl group, the alkene group, the heterocyclic group, the aryl group, and the cycloalkyl group of $R^7$ and $R^9$ may be substituted with 1 to 5 substituents independently selected from halogen, hydroxy, amino, nitro, cyano, carboxy, an alkyl group having 1 to 8 carbons, an alkoxy group having 1 to 8 carbon atoms, and a heterocyclic group having 3 to 10 carbon atoms; and $R^8$ may be selected from an optionally substituted alkylene group having 1 to 8 carbon atoms, an optionally substituted alkenylene group having 2 to 8 carbon atoms, an optionally substituted divalent heterocyclic group with 3 to 6 carbon atoms, an optionally substituted arylene group having 6 to 9 carbon atoms and an optionally substituted cycloalkylene group having 3 to 8 carbon atoms; and the alkylene group, the alkenylene group, the divalent heterocyclic group, the arylene group, and the cycloalkylene group may be substituted with 1 to 4 substituents independently selected from a halogen, hydroxy, amino, nitro, cyano, carboxy, an alkyl group having 1 to 8 carbons, an alkoxy group having 1 to 8 carbon atoms, and a heterocyclic group having 3 to 10 carbon atoms.

7. The compound of sentence 1, wherein R, $R^1$, $R^2$, $R^3$, $R^4$, $R^5$, and $R^6$ of Formula (I), and $R^7$ and $R^9$ of Formula (II):

the alkyl group may be selected from a straight or branched chain butyl, pentyl, hexyl, heptyl, octyl, nonyl, decyl, undecyl and dodecyl group, the alkene group may be selected from a vinyl, propenyl, or a straight or branched chain butenyl, pentenyl, hexenyl, heptenyl, octenyl, nonenyl, decenyl, undecenyl and dodecenyl group, the cycloalkyl group may be selected from a cyclopentyl group and a cyclohexyl group, the aryl group may be selected from a phenyl, a tolyl, and a biphenyl group, the heterocyclic group may be selected from pyrrolidine, pyrrole, tetrahydrofuran, furan, tetrahydrothiophene, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, piperidine, pyridine, bipyridine, tetrahydropyran, pyran, piperazine, diazines, morpholine, oxazine, thiomorpholine, and thiazine;

in $R^8$ of Formula (II), the alkylene group may be selected from a straight or branched chain butylene, pentylene, hexylene, heptylene, octylene, nonylene, decylene, undecylene and dodecylene group, the alkenylene group may be selected from a vinylene, propenylene, or a straight or branched chain butenylene, pentenylene, hexenylene, heptenylene, octenylene, nonenylene, decenylene, undecenylene and dodecenylene group, the cycloalkylene group may be selected from a cyclopentylene group and a cyclohexylene group, the arylene group may be selected from a phenylene, a tolylene, and a biphenylene group; and the groups may be optionally substituted with 1-4 substituents and the optional substituents are selected from the group consisting of an alkyl group having 1 to 3 carbons, an aldehyde, a hydroxyl group and methoxy group.

8. In a second aspect, the disclosure relates to an epoxy thermoset prepared by the reaction of a compound containing at least two epoxy groups, and an amine curing agent which may include at least one compound selected from the Formulae (I) and (II):

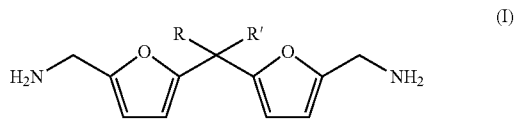

(I)

wherein (i) R may be hydrogen and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

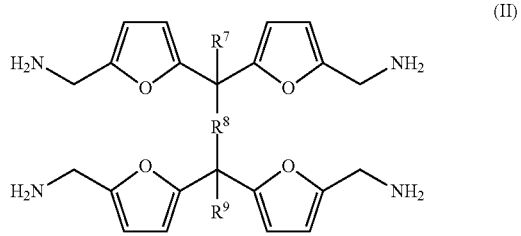

(II)

wherein $R^7$ and $R^9$ may be independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group may be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent may be further substituted with hydroxy, an alkoxy group having 1 to 20 carbon atoms, or an alkylamino group having 1 to 2 carbon atoms; and $R^8$ may be an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; and the alkylene group, the alkenylene group, the divalent heterocyclic group, the arylene group, and the cycloalkylene group of $R^8$ may be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

9. The epoxy thermoset of sentence 8, wherein the amine curing agent may be selected from the compound of any one of sentences 1-7.

10. The epoxy thermoset of sentence 8, wherein R may be hydrogen and $R^1$ may be an alkyl group having 4 to 20 carbon atoms, 7 to 20 carbon atoms, or from 8 to 20 carbon atoms.

11. The compound of sentence 1 or the epoxy thermoset of sentence 8, wherein the compound of Formula (I) or Formula (II) may be prepared from a furfuryl amine and a compound selected from mono-aldehyde, a di-aldehyde, a mono-ketone, a di-ketone, and a poly-aldehyde having three or more aldehyde groups.

12. The compound or epoxy thermoset of sentence 11, wherein the compound of Formula (I) or Formula (II) may be prepared from an aldehyde which has one aldehyde group or a ketone which has one ketone group 13. The compound or epoxy thermoset of sentence 12, wherein Formula (I) or Formula (II) may be prepared from an aldehyde or ketone selected from 3,4-dihydroxy-benzaldehyde, vanillin (4-hydroxy-3-methoxy-benzaldehyde), 4-formyl-2-hydroxyl-phenol, 4-formyl-2-methoxy-phenol, 3,4,5-trihydroxy-benzaldehyde, furfural, cuminaldehyde, cinnamaldehyde, citral, anisaldehyde, 2-heptanone, acetophenone, ethyl phenyl ketone, 2-furyl methyl ketone, succinaldehyde, glutaraldehyde, terephthaldehyde, furan 2,5-dialdehyde, 1,1'-biphenyl-4,4'-dicaboxaldehyde, 2,2'-bipryridyl-5,5'-dialdehyde, curcumin, and

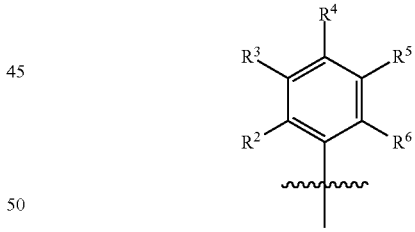

wherein n=0-10, and each —$CH_2$— group may be optionally substituted with one or two $C_1$-$C_6$ alkyl groups; or an ester or ether thereof. In the foregoing embodiment, the furfuryl amine, aldehyde and ketone starting materials may be isolated from bio-based resources.

14. The epoxy thermoset of sentence 8, wherein $R^1$ may be a phenyl group having the following structure:

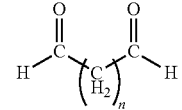

wherein

represents the attachment point to the methylene carbon bridging the furan rings; and $R^2$, $R^3$, $R^4$, $R^5$, and $R^6$ may be independently selected from hydrogen, a hydroxyl group, an alkoxy group having 1 to 20 carbon atoms, an optionally substituted alkyl group having 1 to 20 carbon atoms, an optionally substituted alkene group having 2 to 20 carbon atoms, an optionally substituted aryl group having 3 to 10 carbon atoms, an optionally substituted heterocyclic group having 3 to 9 carbon atoms, and an optionally substituted cycloalkyl group having 3 to 12 carbon atoms; and the alkyl group, the alkene group, the aryl group, the heterocyclic group, and the cycloalkyl group may be substituted with 1 to 5 substituents independently selected from a hydroxyl group, an alkoxy group having 1 to 10 carbon atoms, and a heterocyclic group having 3 to 15 carbon atoms. In the foregoing embodiment, $R^1$ may be selected from a cyclohexyl group, a $C_3$-$C_{20}$ alkyl group substituted with a diamino difuran group and an alkyl group having 3-20 carbon atoms; or wherein the furfuryl amine, aldehyde and ketone starting materials may be isolated from bio-based resources.

15. The epoxy thermoset of sentence 8, wherein $R^2$ and $R^6$ may be hydrogen, $R^3$ and $R^5$ may be independently selected from hydrogen and an alkoxy group, and $R^4$ may be selected from hydrogen, a hydroxyl group, an alkyl group and an alkoxy group. In the foregoing embodiment, $R^1$ may be selected from a cyclohexyl group, a $C_3$-$C_{20}$ alkyl group substituted with a diamino difuran group and an alkyl group having 3-20 carbon atoms.

16. The epoxy thermoset of sentence 8, wherein $R^2$, $R^3$, $R^5$ and $R^6$ may be hydrogen and $R^4$ may be a $C_1$-$C_{20}$ alkyl group substituted with a diamino difuran group.

17. The epoxy thermoset of sentence 8, wherein $R^1$ may be selected from an optionally substituted alkyl group or having 3 to 20 carbon atoms and an optionally substituted cycloalkyl group having 3 to 12 carbon atoms; the alkyl or the cycloalkyl group may be substituted with 1 to 5 substituents independently selected from a heterocyclic group, a hydroxyl group, and an alkoxy group having 1 to 20 carbon atoms, and the heterocyclic group may be further substituted with an alkylamino group having 1 to 20 carbon atoms.

18. The epoxy thermoset of any one of sentences 8, 14, and 15, wherein $R^1$ may be selected from a cyclohexyl group, a $C_3$-$C_{20}$ alkyl group substituted with a diamino difuran group and an alkyl group having 3-20 carbon atoms.

19. The epoxy thermoset of sentence 8, wherein the amine curing agent may be selected from the group consisting of 4-{bis[5-(aminomethyl)furan-2-yl]methyl}-2-methoxyphenol, 4-{bis[5-(aminomethyl)furan-2-yl]methyl}-2,6-dimethoxyphenol, {[(3,4-dimethoxyphenyl)methanediyl]difuran-5,2-diyl}dimethanamine, 4-{bis[5-(aminomethyl) furan-2-yl]methyl}phenol, [(phenylmethanediyl)difuran-5,2-diyl]dimethanamine, {[(4-methylphenyl)methanediyl] difuran-5,2-diyl}dimethanamine, ({[4-(propan-2-yl)phenyl] methanediyl}difuran-5,2-diyl)dimethanamine, [(cyclohexylmethanediyl)difuran-5,2-diyl]dimethanamine, (octane-1,1-diyldifuran-5,2-diyl)dimethanamine, (dodecane-1,1-diyldifuran-5,2-diyl)dimethanamine, (methanetriyl))tetrakis(furan-5,2-diyl))tetramethanamine, and (5,5', 5'',5'''-(pentane-1,1,5,5-tetrayl)tetrakis(furan-5,2-diyl)) tetramethanamine, and the compound containing at least two epoxy groups may be (5,5',5'',5'''-(1,4-phenylenebis(methylglycidyl ether).

20. The epoxy thermoset of any one of sentences 8 to 19, wherein the epoxy thermoset may have a mole ratio of amino groups in the amine curing agent to the epoxy groups of from about 0.8 to 2.5, or from about 1 to 2.

21. The epoxy thermoset of any one of sentences 8 to 17, wherein the epoxy group-containing compound may be selected from bisphenol A epoxy resin, bisphenol F epoxy resin, novolac epoxy resin, aliphatic epoxy resin, glycidylamine epoxy resin, bisguaiacol, a diglycidyl ether having a bisphenol alkylene bridge (bisphenol A, B, C, D, or E), tetraglycidyl diamino diphenyl methane (TGDDM), and a diglycidyl ether having a bisphenol sulfone bridge (bisphenol S), and the reaction may optionally include mono epoxies, which are preferably phenyl glycidyl ether.

22. The epoxy thermoset of sentence 21, wherein the epoxy group-containing compound may be a bisphenol-A diglycidyl ether (DGEBA) epoxy resin compound or an oligomer thereof.

23. The epoxy thermoset of any one of sentences 13-15, wherein the furfuryl amine, aldehyde and ketone starting materials may be isolated from bio-based resources.

24. The epoxy thermoset of any one of sentences 8 to 23, wherein the amine curing agent may be less mutagenic and toxic than phenolic amines.

25. In a third aspect, the disclosure relates to a method of making a polymer including a step of curing a composition comprising a compound containing at least two epoxy groups, and the amine curing agent as defined in any one of the sentences 8-19.

26. In a fourth aspect, the disclosure relates to a polymer obtained by the method of sentence 25.

27. The polymer of sentence 26, wherein the polymer may have a glass transition temperature ($T_g$) range of from 0° C. to 200° C.

28. The polymer of sentence 26, wherein the polymer may have a water uptake of no more than 5.9 wt. %, or 0.25 wt. % to 4.0 wt. %, or 0.4 wt. % to 2.6 wt. %.

29. The polymer of sentence 26, wherein the polymer may have a density of at least 1.0 g/cm$^3$, or 1.05 g/cm$^3$ to 1.8 g/cm$^3$, or 1.1 to 1.4 g/cm$^3$.

30. In a fifth aspect, the disclosure relates to a polymer composition including the polymer of any one of the sentences 8-29, and may further including one or more of fibers, clays, silicates, fillers, whiskers, pigments, corrosion inhibitors, flow additives, film formers, defoamers, coupling agents, antioxidants, stabilizers, flame retardants, reheating aids, plasticizers, flexibilizers, anti-fogging agents, nucleating agents, or combinations thereof.

31. The polymer composition of sentence 30, wherein the polymer composition may further include pigment, corrosion inhibitor and fibers, wherein the pigment may be selected from titanium dioxide, iron oxides, carbon black and mixtures thereof; the corrosion inhibitor may be zinc phosphate; and the fibers may be glass fibers and carbon fibers.

32. The compound of sentence 1 and the polymer of sentence 26, wherein R may be hydrogen and $R^1$ may be a phenyl group with at least one electron donating group and an aromatic structure having more electron donating character than electron withdrawing character.

33. In a sixth aspect, the disclosure relates to a method of indicating the pH of a system, wherein the method may include contacting a compound or polymer of sentence 32, with a composition and evaluating the ultraviolet visible spectrum of the composition after it has been contacted with the compound or polymer as described in the foregoing embodiment.

34. In a seventh aspect, the disclosure relates to a polyurea thermoplastic prepared by the reaction of a compound containing two isocyanate groups, and an amine curing agent which may include at least one compound selected from the Formulae (I) and (II):

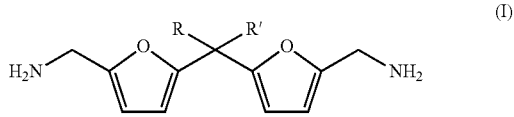
(I)

wherein (i) R may be hydrogen and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms.

35. The polyurea of sentence 34, wherein the amine monomer may be selected from a diamine compound of the foregoing embodiment.

36. In an eighth aspect, the disclosure relates to a polyamide thermoplastic prepared by the reaction of: a compound containing two carboxylic acid groups or two acyl chloride groups, or acid chloride, methyl ester or $C_{2-12}$ alkyl ester thereof, and an amine curing agent which includes at least one compound selected from the Formulae (I) and (II):

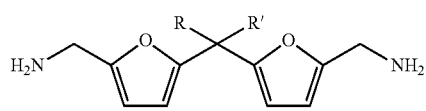

(I)

wherein (i) R may be hydrogen and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms.

37. The polyamide of sentence 36, wherein the amine monomer may be selected from a diamine compound as described in the foregoing embodiment.

38. In a ninth aspect, the disclosure relates to a polyurea thermoset prepared by the reaction of: a compound containing at least two isocyanate groups, and an amine curing agent which includes at least one compound selected from the Formulae (I) and (II):

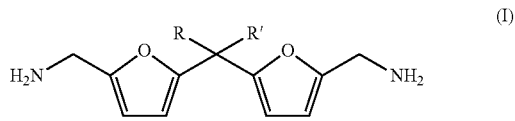

(I)

wherein (i) R may be hydrogen and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

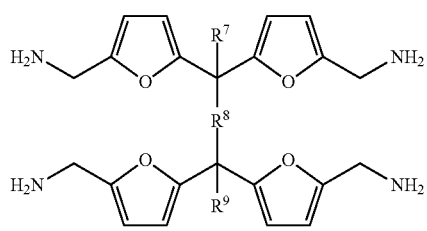

(II)

wherein $R^7$ and $R^9$ may be independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ may be an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; and the alkylene group, the alkenylene group, the divalent heterocyclic group, the arylene group, and the cycloalkylene group of $R^8$ may be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

39. The polyurea thermoset of sentence 38, the amine curing agent may be selected from the compound as described in any one of sentences 1-7.

40. In a tenth aspect, the disclosure relates to an epoxy derivative wherein the difuran diamine of Formula (I) of embodiment 1 may be substituted on the terminal amino groups with alkyl epoxy groups as follows:

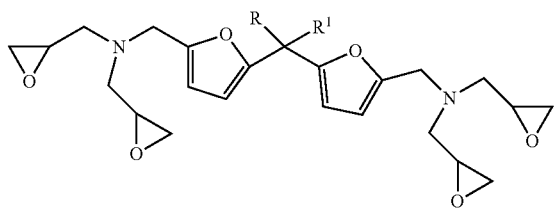

wherein R and $R^1$ are as defined in embodiment 1, and the tetrafuran tetraamine of Formula (II) of embodiment 1 is substituted on the terminal amino groups with alkyl epoxy groups as follows:

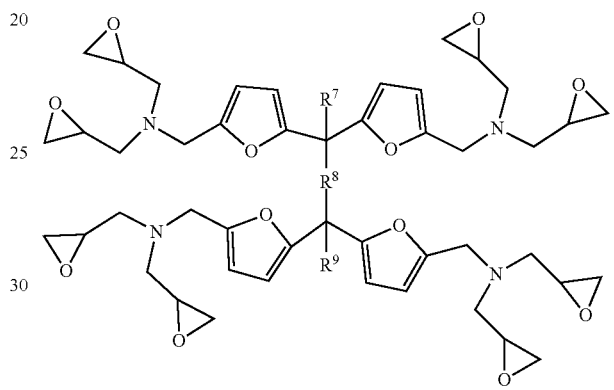

wherein $R^7$, $R^8$, and $R^9$ may be as defined in sentence 1.

41. In an eleventh aspect, the disclosure relates to a method of preparing the epoxy derivative as described in sentence 40, via reaction with excess epichlorohydrin at 40° C.-50° C. with 0.5-5 wt. % tetrabutylammonium bromide for 3 hours, followed by dropwise addition of 40 wt. % NaOH in water followed by extraction of salts and drying.

42. In a twelfth aspect, the disclosure relates to epoxy amine polymers prepared via the reaction of the epoxy derivatives as described in sentence 40 with at least one diamine, triamine, or tetraamine, including the diamine and tetraamine of sentences 1-7, as described in sentences 8-29.

43. In a thirteenth aspect, the disclosure relates to a thermoplastic Michael addition product prepared by the reaction of: a compound containing two methacrylate and/or acrylate groups, and an amine curing agent which comprises at least one compound selected from the Formulae (I):

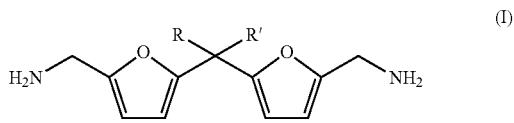

(I)

wherein (i) R may be hydrogen and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms;

and the alkyl group, the alkene group, the cycloalkyl group, the aryl group and the heterocyclic group of R and $R^1$ may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms.

44. The thermoplastic Michael addition product of sentence 43, wherein the amine monomer may be selected from a diamine compound of the sentence 43.

45. In a fourteenth aspect, the disclosure relates to a thermoset Michael addition product prepared by the reaction of: a compound containing at least two methacrylate and/or acrylate groups, and an amine curing agent which comprises at least one compound selected from the Formulae (I): and (II):

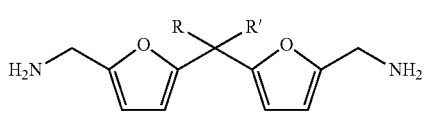
(I)

wherein (i) R may be hydrogen and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R may be selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ may be selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ may be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

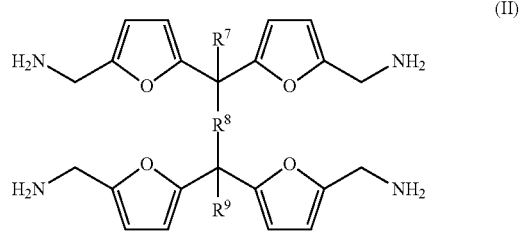
(II)

wherein $R^7$ and $R^9$ may be independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ may be an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; and the alkylene group, the alkenylene group, the divalent heterocyclic group, the arylene group, and the cycloalkylene group of $R^8$ may be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

46. In a fifteenth aspect, the disclosure relates to an isocyanate derivative of the following formulae:

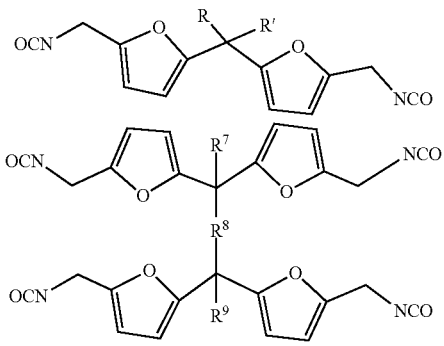

wherein R, $R^1$, $R^7$, $R^8$, and $R^9$ may be according to definition of sentence 1.

47. In a sixteenth aspect, the disclosure relates to a polyurethane polymer prepared by the reaction of at least one of the isocyanate derivative of sentence 46, with at least one polyol.

48. In a seventeenth aspect, the disclosure relates to a polyurea polymer prepared by the reaction of at least one of the isocyanate derivatives according to sentence 46, with at least one diamine, triamine, or tetraamine, including the diamine and tetraamines of sentences 1-7, as described in sentences 8-29.

Herein, we disclose versatile, renewable furan based amines curing agents for the preparation of hydrophobic resins with superior thermomechanical properties. The incorporated aromatic and aliphatic substituents in between the furan bridge structure of amine monomers result in higher thermomechanical and lower water uptake properties in developed epoxy-amine networks. The results of the present invention show the unique advantages of renewable furan based amine monomers over commonly-used curing agents.

DETAILED DESCRIPTION OF THE PREFERRED EMBODIMENTS

Figure 1:
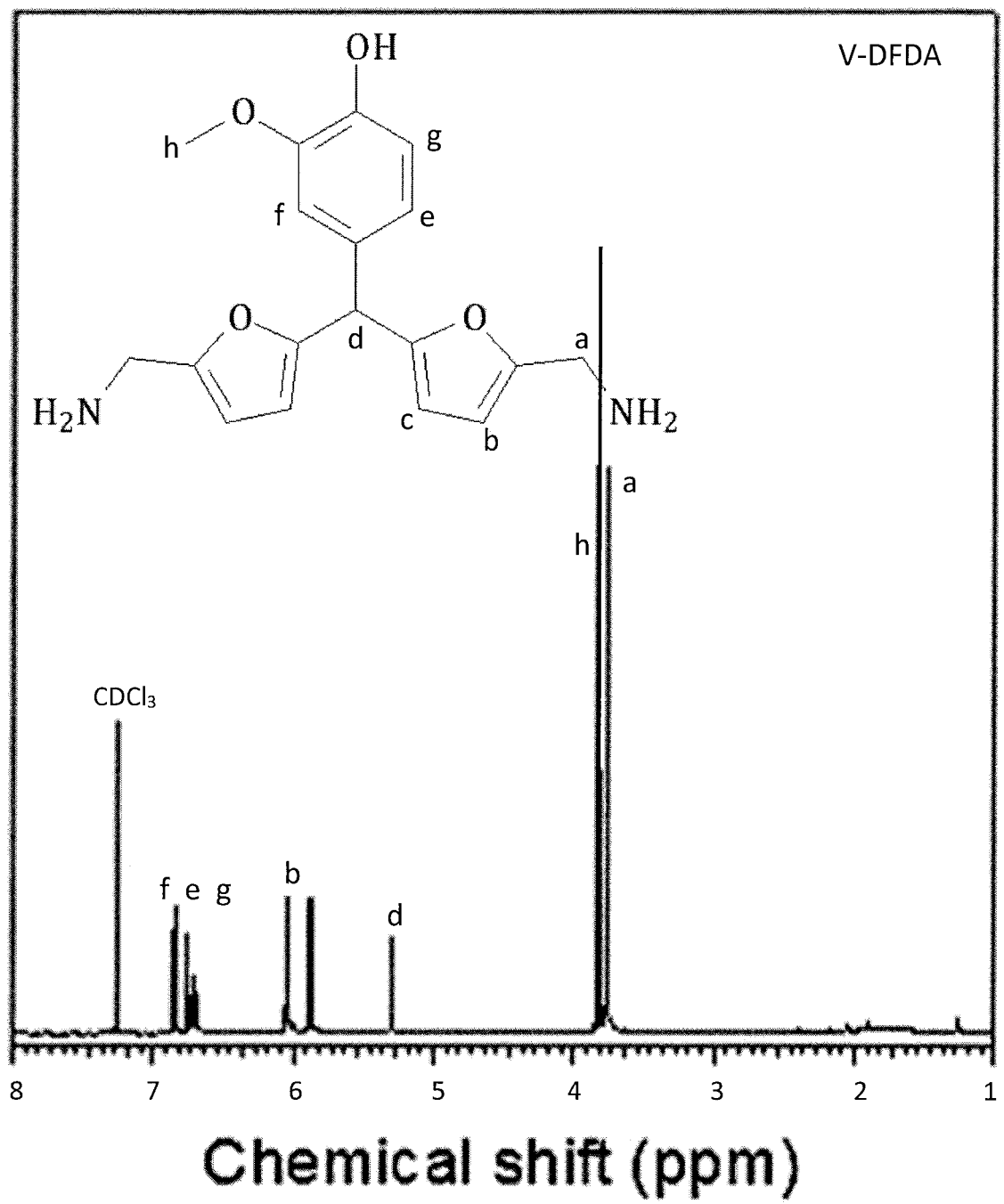
FIG. 1 shows the $^1$H NMR spectra of 4-{bis[5-(aminomethyl)furan-2-yl]methyl}-2-methoxyphenol (V-DFDA).
Figure 2:
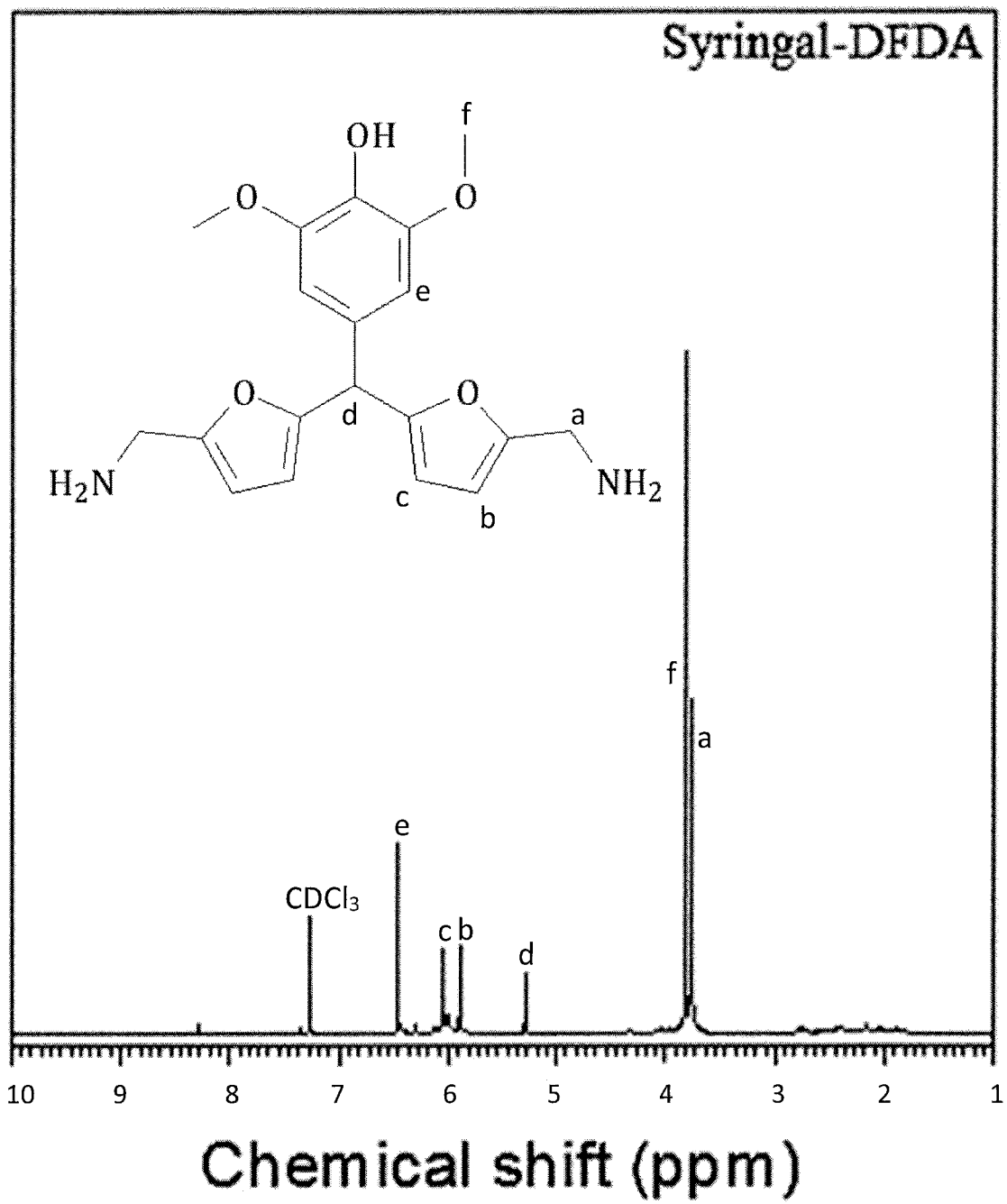
FIG. 2 shows the $^1$H NMR spectra of 4-{bis[5-(aminomethyl)furan-2-yl]methyl}-2,6-dimethoxyphenol (Syringal-DFDA).

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

As used herein and in the appended claims, the singular forms "a", "an", and "the" include plural references unless the context clearly dictates otherwise. The terms "a" (or "an"), "one or more" and "at least one" can be used interchangeably herein. It is also to be noted that the terms "comprising", "including", and "having" can be used interchangeably.

Disclosed herein is a furan containing compound and polymers, thermosets, thermoplastics including the furan containing compound therein.

The Furan Containing Compound

In one embodiment, the furan containing compound of the disclosure may be selected from compounds of the following Formulae (I) and (II):

(A) difuran diamines of the Formula (I),

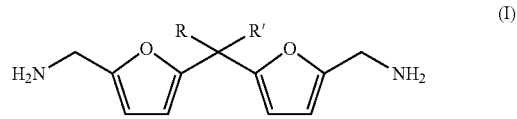

wherein
(i) R is hydrogen and $R^1$ is selected from an optionally substituted alkyl group having 4 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; the alkyl group, the alkene group, the cycloalkyl group, the aryl group and the heterocyclic group of $R^1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms, and when $R^1$ is a phenyl group, the phenyl group must be substituted; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ can be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms; or (iii) R is selected from hydrogen, an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; the alkyl group, the alkene group, the cycloalkyl group, the aryl group and the heterocyclic group of R can be substituted with 1 to 5 substituents independently selected from a halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ is a phenyl group of the following structure:

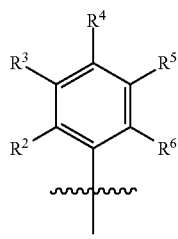

wherein

represents the attachment point to the methylene carbon bridging the furan rings in Formula (I); $R^2$, $R^3$, $R^4$, $R^5$, and $R^6$ are independently selected from hydrogen, a hydroxyl group, an alkoxy group having 1 to 20 carbon atoms, an optionally substituted alkyl group having 1 to 20 carbon atoms, an optionally substituted alkene group having 2 to 20 carbon atoms, an optionally substituted aryl group having 6 to 10 carbon atoms, an optionally substituted heterocyclic group having 3 to 9 carbon atoms, and an optionally substituted cycloalkyl group having 3 to 12 carbon atoms; the alkyl group, the alkene group, the aryl group, the heterocyclic group, and the cycloalkyl group of $R^2$, $R^3$, $R^4$, $R^5$, and $R^6$ can be substituted with 1 to 5 substituents independently selected from halogen, hydroxy, amino, nitro, cyano, carboxy, an alkyl group having 1 to 20 carbons, an alkoxy group, and a heterocyclic group having 1 to 20 carbon atoms; and when R is hydrogen, at least one of $R^2$, $R^3$, $R^4$, $R^5$ and $R^6$ is not hydrogen; and B) a tetrafuran tetra amine of the Formula (II),

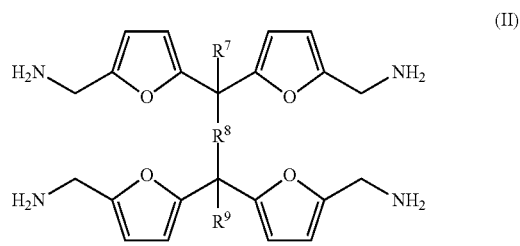

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group of $R^7$ and $R^9$ can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; the alkylene group, the alkenylene group, the divalent heterocyclic group, the arylene group, and the cycloalkylene group of $R^8$ can be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

In another embodiment, R and $R^1$ may be independently selected from hydrogen, an optionally substituted alkyl group having 7 to 20 carbon atoms, an optionally substituted alkene group having 3 to 20 carbon atoms, an optionally substituted cycloalkyl group having 3 to 12 carbon atoms and a phenyl group of the following structure:

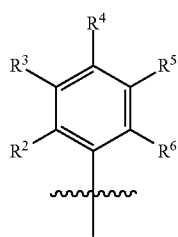

and the alkyl group, the alkene group, and the cycloalkyl group of R and $R^1$ can be substituted with 1 to 5 substituents independently selected from a heterocyclic group having 3 to 16 carbons, a hydroxyl group, and an alkoxy group having 1 to 20 carbon atoms;

represents the attachment point to the methylene carbon bridging the furan rings in the Formula (I); $R^2$, $R^3$, $R^4$, $R^5$, and $R^6$ are independently selected from hydrogen, a hydroxyl group, an alkoxy group having 1 to 20 carbon atoms, an optionally substituted alkyl group having 1 to 20 carbon atoms, an optionally substituted alkene group having 2 to 20 carbon atoms, an optionally substituted aryl group having 6 to 10 carbon atoms, an optionally substituted heterocyclic group having 3 to 9 carbon atoms, and an optionally substituted cycloalkyl group having 3 to 12 carbon atoms; the alkyl group, the alkene group, the aryl group, the heterocyclic group, and the cycloalkyl group of $R^2$, $R^3$, $R^4$, $R^5$, and $R^6$ can be substituted with 1 to 5 substituents independently selected from a hydroxyl group, an alkoxy group, and a heterocyclic group having 1 to 20 carbon atoms; wherein at least one of $R^2$, $R^3$, $R^4$, $R^5$ and $R^6$ is not a hydrogen when one of R and $R^1$ is hydrogen, and wherein only one of R and $R^1$ can be hydrogen.

In another embodiment, R is hydrogen; $R^1$ is selected from a phenyl group of the following structure:

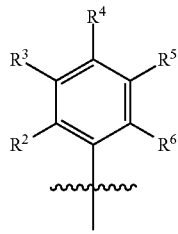

wherein

represents the attachment point to the methylene carbon bridging the furan rings in Formula (I); $R^2$, $R^3$, $R^4$, $R^5$, and $R^6$ are independently selected from hydrogen, a hydroxyl group, an alkoxy group having 1 to 4 carbon atoms, an alkyl group having 1 to 6 carbon atoms, and an alkene group having 2 to 4 carbon atoms; and at least one of $R^2$, $R^3$, $R^4$, $R^5$ and $R^6$ is not hydrogen.

In another embodiment, R and $R^1$ are each independently selected from hydrogen, an optionally substituted alkyl group having 8 to 18 carbon atoms, an optionally substituted alkene group having 4 to 18 carbon atoms, and an optionally substituted cycloalkyl group having 3 to 8 carbon atoms, the alkyl group, the alkene group, and the cycloalkyl group of R and $R^1$ can be substituted with 1 to 5 substituents independently selected from halogen, hydroxy, amino, nitro, cyano, carboxy, an alkyl group having 1 to 8 carbons, and an alkoxy group having 1 to 8 carbon atoms; and only one of R and $R^1$ can be hydrogen.

In another embodiment, the furan containing compound is a tetrafuran tetraamine compound of Formula (II):

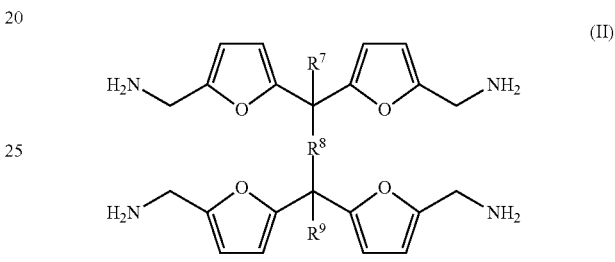

wherein $R^7$ and $R^9$ are independently selected from hydrogen, an optionally substituted alkyl group having 1 to 18 carbon atoms, or from 1 to 8, an optionally substituted alkene group having 2 to 18 carbon atoms, or from 2 to 8 carbon atoms, an optionally substituted heterocyclic group with 3 to 8 carbon atoms, an optionally substituted aryl group having 6 to 9 carbon atoms and an optionally substituted cycloalkyl group having 3 to 12 carbon atoms, or from 3 to 8 carbon atoms; and the alkyl group, the alkene group, the heterocyclic group, the aryl group, and the cycloalkyl group of $R^7$ and $R^9$ can be substituted with 1 to 5 substituents independently selected from halogen, hydroxy, amino, nitro, cyano, carboxy, an alkyl group having 1 to 8 carbons, an alkoxy group having 1 to 8 carbon atoms, and a heterocyclic group having 3 to 10 carbon atoms; and $R^8$ is selected from an optionally substituted alkylene group having 1 to 18 carbon atoms, or from 1 to 8 carbon atoms, an optionally substituted alkenylene group having 2 to 18 carbon atoms, or from 2 to 8 carbon atoms, an optionally substituted divalent heterocyclic group with 3 to 8 carbon atoms, or from 3 to 6 carbon atoms, and an optionally substituted arylene group having 6 to 9 carbon atoms and an optionally substituted cycloalkylene group having 3 to 12 carbon atoms, or from 3 to 8 carbon atoms; and the alkylene group, the alkenylene group, the divalent heterocyclic group, the arylene group, and the cycloalkylene group of $R^8$ can be substituted with 1 to 4 substituents independently selected from halogen, hydroxy, amino, nitro, cyano, carboxy, an alkyl group having 1 to 8 carbons, an alkoxy group having 1 to 8 carbon atoms, and a heterocyclic group having 3 to 10 carbon atoms.

In another embodiment of the invention, R, $R^1$, $R^2$, $R^3$, $R^4$, $R^5$, and $R^6$ of Formula (I), and $R^7$ and $R^9$ of Formula (II), the alkyl group is selected from a straight or branched chain butyl, pentyl, hexyl, heptyl, octyl, nonyl, decyl, undecyl and dodecyl group, the alkene group is selected from a vinyl, propenyl, or a straight or branched chain butenyl, pentenyl, hexenyl, heptenyl, octenyl, nonenyl, decenyl, undecenyl and dodecenyl group, the cycloalkyl group is selected from a cyclopentyl group and a cyclohexyl group, the aryl group is selected from a phenyl, a tolyl, and a biphenyl group, the heterocyclic group is selected from pyrrolidine, pyrrole, tetrahydrofuran, furan, tetrahydrothiophene, thiophene, imidazolidine, pyrazolidine, imidazole, pyrazole, oxazolidine, isoxazolidine, oxazole, isoxazole, thiazolidine, isothiazolidine, thiazole, isothiazole, dioxolane, dithiolane, piperidine, pyridine, bipyridine, tetrahydropyran, pyran, piperazine, diazines, morpholine, oxazine, thiomorpholine, and thiazine; in $R^8$ of Formula (II), the alkylene group is selected from a straight or branched chain butylene, pentylene, hexylene, heptylene, octylene, nonylene, decylene, undecylene and dodecylene group, the alkenylene group is selected from a vinylene, propenylene, or a straight or branched chain butenylene, pentenylene, hexenylene, heptenylene, octenylene, nonenylene, decenylene, undecenylene and dodecenylene group, the cycloalkylene group is selected from a cyclopentylene group and a cyclohexylene group, the arylene group is selected from a phenylene, a tolylene, and a biphenylene group; and the groups are optionally substituted with 1-4 substituents and the optional substituents are selected from the group consisting of an alkyl group having 1 to 3 carbons, an aldehyde, a hydroxyl group and methoxy group.

Epoxy Thermosets

In one aspect of the present invention, the amine based furan compounds are amine curing agents for preparing epoxy thermosets. The amine curing agents may be reacted with an epoxy-containing compound with at least two epoxy groups to form an epoxy thermoset. The amine curing agents used for preparing epoxy thermosets may be selected from the furan containing compounds of the Formulae (I) and (II). The amine curing agent may be present in an amount such that the molar ratio of amino groups in the amine curing agent to the epoxy groups is from about 0.8 to 2.5, or from about 1 to 2.

In one embodiment, the epoxy thermoset may be prepared by reaction of: a compound containing at least two epoxy groups, and an amine curing agent which comprises at least one compound selected from the Formulae (I) and (II):

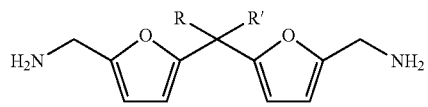

(I)

wherein (i) R is hydrogen and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

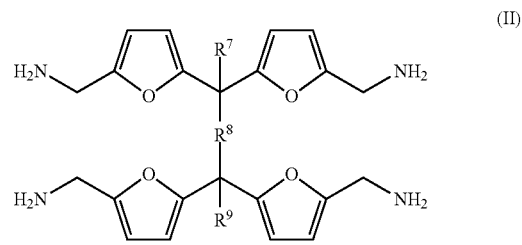

(II)

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to carbon atoms and an optionally substituted cycloalkylene group having 3 to 12 carbon atoms; and the alkylene group, the alkenylene group, the divalent heterocyclic group, the arylene group, and the cycloalkylene group of $R^8$ can be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

In the foregoing embodiment, $R^1$ may be selected from an optionally substituted alkyl group or having 3 to 20 carbon atoms and an optionally substituted cycloalkyl group having 3 to 12 carbon atoms; the alkyl or the cycloalkyl group can be substituted with 1 to 5 substituents independently selected from a heterocyclic group, a hydroxyl group, and an alkoxy group having 1 to 20 carbon atoms, and the heterocyclic group can be further substituted with an alkylamino group having 1 to 20 carbon atoms; or $R^1$ is selected from a cyclohexyl group, a $C_3$-$C_{20}$ alkyl group substituted with a diamino difuran group and an alkyl group having 3-20 carbon atoms. Alternatively, R is hydrogen and $R^1$ may be an alkyl group having 4 to 20 carbon atoms, 7 to 20 carbon atoms, or from 8 to 20 carbon atoms.

In one embodiment, the compound of formula (I) or Formula (II) is prepared from a furfuryl amine and a compound selected from an aldehyde or ketone. The aldehydes or ketones may be selected from mono-aldehydes, di-aldehydes, mono-ketones, di-ketones, and a poly-aldehyde having three or more aldehyde groups. Suitable aldehydes and ketones of the present invention may be selected from aldehyde or ketone selected from 3,4-dihydroxy-benzaldehyde, vanillin (4-hydroxy-3-methoxy-benzaldehyde), 4-formyl-2-hydroxyl-phenol, 4-formyl-2-methoxy-phenol, 3,4,5-trihydroxy-benzaldehyde, furfural, cuminaldehyde, cinnamaldehyde, citral, anisaldehyde, 2-heptanone, acetophenone, ethyl phenyl ketone, 2-furyl methyl ketone, succinaldehyde, glutaraldehyde, terephthaldehyde, furan 2,5-dialdehyde, 1,1'-biphenyl-4,4'-dicaboxaldehyde, 2,2'-bipryridyl-5,5'-dialdehyde, curcumin, and

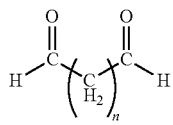

wherein n=0-10, and each —$CH_2$— group may be optionally substituted with one or two $C_1$-$C_6$ alkyl groups; or an ester or ether thereof.

In certain embodiments, the mono-aldehyde is not selected from formaldehyde, paraformaldehyde, or acetone. In certain embodiments, the furfuryl amine, aldehyde and ketone starting materials are isolated from bio-based resources. In certain embodiments the amine curing agent is less mutagenic and toxic than phenolic amines.

In another embodiment, $R_1$ is a phenyl group having the following structure:

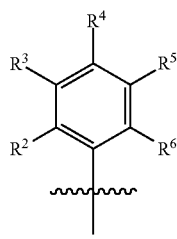

wherein

represents the attachment point to the methylene carbon bridging the furan rings; and $R^2$, $R^3$, $R^4$, $R^5$, and $R^6$ are independently selected from hydrogen, a hydroxyl group, an alkoxy group having 1 to 20 carbon atoms, an optionally substituted alkyl group having 1 to 20 carbon atoms, an optionally substituted alkene group having 2 to 20 carbon atoms, an optionally substituted aryl group having 3 to 10 carbon atoms, an optionally substituted heterocyclic group having 3 to 9 carbon atoms, and an optionally substituted cycloalkyl group having 3 to 12 carbon atoms; and the alkyl group, the alkene group, the aryl group, the heterocyclic group, and the cycloalkyl group can be substituted with 1 to 5 substituents independently selected from a hydroxyl group, an alkoxy group having 1 to 10 carbon atoms, and a heterocyclic group having 3 to 15 carbon atoms. Preferably, $R^2$ and $R^6$ are hydrogen, and $R^3$ and $R^5$, are independently selected from hydrogen and an alkoxy group, and $R^4$ is selected from hydrogen, a hydroxyl group, an alkyl group and an alkoxy group. Even more preferably, $R^2$, $R^3$, $R^5$, and $R^6$ are hydrogen, and $R^4$ is a $C_1$-$C_{20}$ alkyl group substituted with a diamino difuran group.

Suitable epoxy group-containing compounds may be selected from bisphenol A epoxy resin, bisphenol F epoxy resin, novolac epoxy resin, aliphatic epoxy resin, glycidylamine epoxy resin, bisguaiacol, a diglycidyl ether having a bisphenol alkylene bridge (bisphenol A, B, C, D, or E), tetraglycidyl diamino diphenyl methane (TGDDM), and a diglycidyl ether having a bisphenol sulfone bridge (bisphenol S), and the reaction optionally includes mono epoxies, which are preferably phenyl glycidyl ether. Preferably, the epoxy-containing compound is bisphenol-A diglycidyl ether (DGEBA) epoxy resin compound or an oligomer thereof.

In a preferred embodiment, the amine curing agent is selected from the group consisting of 4-{bis[5-(aminomethyl)furan-2-yl]methyl}-2-methoxyphenol, 4-{bis[5-(aminomethyl)furan-2-yl]methyl}-2,6-dimethoxyphenol, {[(3,4-dimethoxyphenyl)methanediyl]difuran-5,2-diyl}dimethanamine, 4-{bis[5-(aminomethyl)furan-2-yl]methyl}phenol, [(phenylmethanediyl)difuran-5,2-diyl]dimethanamine, {[(4-methylphenyl)methanediyl]difuran-5,2-diyl}dimethanamine, ({[4-(propan-2-yl)phenyl]methanediyl}difuran-5,2-diyl)dimethanamine, [(cyclohexylmethanediyl)difuran-5,2-diyl]dimethanamine, (octane-1,1-diyldifuran-5,2-diyl)dimethanamine, (dodecane-1,1-diyldifuran-5,2-diyl)dimethanamine, (methanetriyl))tetrakis(furan-5,2-diyl))tetramethanamine, and (5,5',5'',5'''-(pentane-1,1,5,5-tetrayl)tetrakis(furan-5,2-diyl)) tetramethanamine, and the compound containing at least two epoxy groups is (5,5',5'',5'''-(1,4-phenylenebis(methylglycidyl ether).

The Polymer

In another aspect, the present disclosure relates to a polymer, wherein the polymer is prepared by the following step a) curing a composition comprising a compound containing at least two epoxy groups with the furan-containing compound, wherein the furan-containing compound is an amine curing agent, as set forth above.

The polymer may have a glass transition temperature ($T_g$) range of from 0° C. to 200° C., or a water uptake of no more than 5.9 wt. %, or 0.25 wt. % to 4.0 wt. %, or 0.4 wt. % to 2.6 wt. %, or a density of at least 1.0 g/cm³, or 1.05 g/cm³ to 1.8 g/cm³, or 1.1 to 1.4 g/cm³.

In certain embodiments, the present disclosure relates to a polymer composition which may include the aforementioned polymer, and further includes one or more of fibers, clays, silicates, fillers, whiskers, pigments, corrosion inhibitors, flow additives, film formers, defoamers, coupling agents, antioxidants, stabilizers, flame retardants, reheating aids, plasticizers, flexibilizers, anti-fogging agents, nucleating agents, or combinations thereof. In a preferred embodiment, the polymer composition includes pigments, corrosion inhibitors, and fibers, wherein the pigment is selected from titanium dioxide, iron oxides, carbon black and mixtures thereof; the corrosion inhibitor is zinc phosphate; and the fibers are selected from glass fibers and carbon fibers.

In a preferred embodiment of the furan-containing compound and the polymer, R is hydrogen and $R^1$ is a phenyl group with at least one electron donating group and the aromatic structure has more electron donating character than electron withdrawing character.

The present invention also relates to a method of indicating the pH of a system, where the method comprises contacting a compound or polymer as set forth above, with a composition and evaluating the ultraviolet visible spectrum of the composition after it has been contacted with the furan containing-compound or polymer. Methyne protons vicinal to three aromatic groups are relatively acidic because the remaining electrons can be shared among the three aromatic groups maintaining the stability of the monomer. As a result, these protons can be abstracted in alkaline media. When the pH of the media is low enough, the protons can no longer be abstracted. The abstraction of the protons is usually associated with a color change again associated with a change in electronics of close proximity of delocalized electron cloud on the three aromatic rings when these aromatic rings contain at least one electron donating groups and no electron withdrawing groups. This color change enables visible pH detection upon calibration with known standards (pH meter). The furans of the di- and tetra-amine chemicals and polymers serve as two of these monomers. When $R_1$ or $R_8$ is a phenyl group with an electron donating group (e.g., methoxyl, methyl) with no electron withdrawing groups (e.g., nitro), the resulting molecule will likely produce a vibrant color. Its color changes as a result of electronic changes, such as the abstraction of the methyne proton.

Epoxy-Containing Compounds

In one embodiment, the present disclosure may relate to epoxy-containing compounds. An epoxy derivative according to the present invention includes the difuran diamine of Formula (I) which may be substituted on the terminal amino groups with an alkyl epoxy groups as follows:

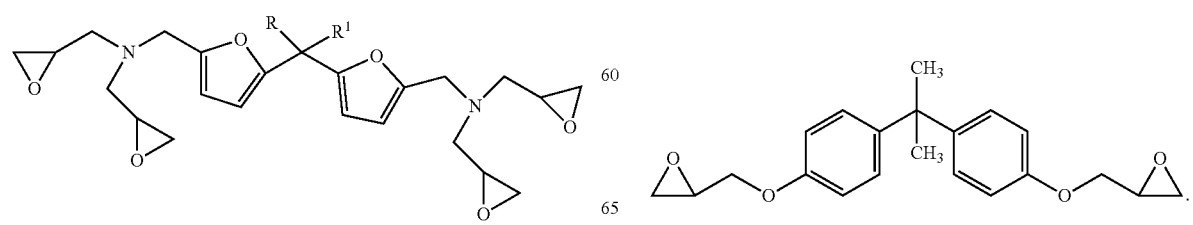

wherein R and $R^1$ are the same as in Formula (I), and the tetrafuran tetraamine of Formula (II) of claim 1 is substituted on the terminal amino groups with alkyl epoxy groups as follows:

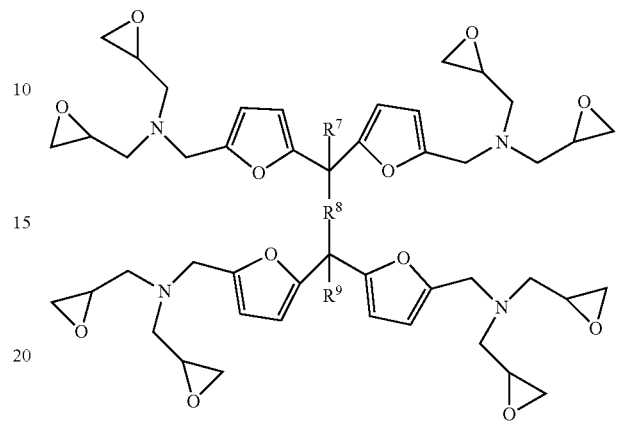

wherein $R^7$, $R^8$, and $R^9$ are as defined as set forth in the furan-containing compound section.

A suitable method for preparing the epoxy derivative may be via reaction with excess epichlorohydrin at 40° C.-50° C. with 0.5 to 5 wt. % tetrabutylammonium bromide for 3 hours followed by dropwise addition of 40 wt. % NaOH in water followed by extraction of salts and drying.

The epoxy derivatives may be used to prepared epoxy amine polymers, prepared via the reaction of the epoxy derivatives with at least one diamine, triamine, or tetramine, including the furan-containing diamine and tetraamines, described herein.

The epoxy-containing compounds of the present invention may be used to make epoxy-amine polymers, epoxy thermosets and include any commercially available epoxy resins, wherein the compound contains at least two epoxy groups. The epoxy-amine polymers may be prepared via the reaction of the epoxy derivative with at least one diamine, triamine, or tetraamine, including the diamine and tetraamine of the furan-containing compounds. Epoxy resins are characterized by containing a 3- membered ring known as an epoxy, epoxide, oxirane or ethoxylene group. Epoxy resin typically contain aliphatic, cycloaliphatic or aromatic backbones. Suitable epoxy resins include, but are not limited to, diglycidyl ether of bisphenol-A, epoxies of the phenolnovolac type and epoxies based on tetrabromobisphenol-A, aliphatic epoxy resin, and glycidylamine epoxy resin.

An example of an epoxy resin is a bisphenol-A diglycidyl ether epoxy resin ("DGEBA", or "BADGE") having the structure:

Another example of an epoxy resin is an oligomer of foregoing molecule, having the chemical structure:

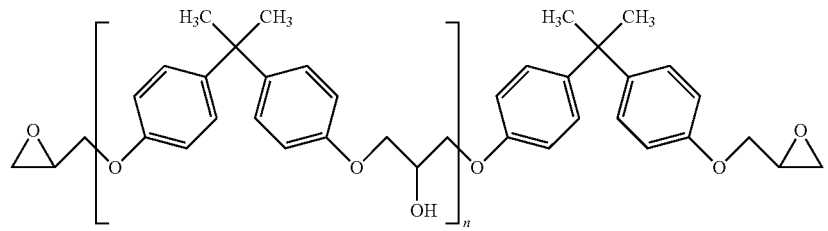

wherein n is a value between 0 and 25.

All of the resins mentioned above may be modified by methods known to skilled persons and still be used in the present invention. Suitable modifications include, but are not limited to, modifications to lower the acid, hydroxyl and/or anhydride number, or to increase flexibility, toughness, or increase the cross-link density of the resin, or to decrease flammability.

In another embodiment, an epoxy thermoset may be prepared by reaction of:
a compound containing at least two epoxy groups, and an amine curing agent which comprises at least one compound selected from the Formulae (I) and (II):

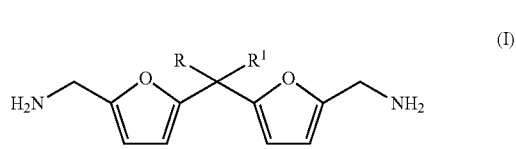
(I)

Wherein (i) R is hydrogen and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R_1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

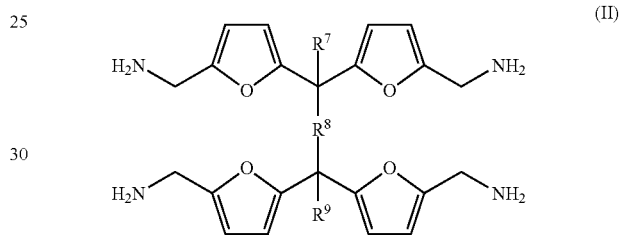
(II)

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; and the alkylene group, the alkenylene group, the divalent heterocyclic group, the arylene group, and the cycloalkylene group of $R^8$ can be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

Isocyanate Derivatives

In one embodiment, the present disclosure may relate to isocyanate derivatives. An isocyanate derivative according to the present invention may be prepared by reacting the difuran diamine compounds or the tetrafuran tetramine compounds with phosgene using a well-known industrial process.

An isocyanate derivative according to the present invention may have the following structure:

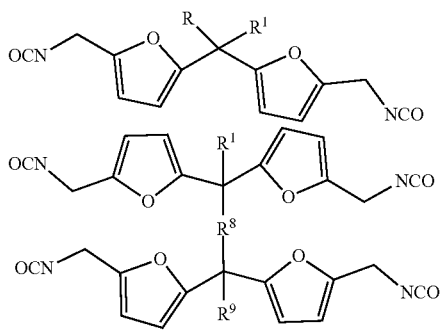

wherein R, $R^1$, $R^7$, $R^8$, and $R^9$ are as set forth above in the furan-containing compound section.

The isocyanate derivatives of the present invention may be used to prepared polyurethane polymers and polyurea polymers.

The polyurea polymer may be prepared by reacting at least one of the isocyanate derivatives with at least one diamine, triamine, or tetraamine, including the diamine and tetraamine of the furan-containing compounds.

The polyurethane polymers may be prepared by reaction of at least one of the isocyanate derivative with at least one polyol. Suitable polyols for preparing the polyurethane include polyether polyols, polyester polyols, polycaprolactone polyols, polycarbonate polyols, glycols and mixtures thereof. Monomeric polyols such as butanediol, 1,6-hexanediol, Bisphenol A and the like, or other higher polyols such as trimethylolpropane, pentaerythritol, and the like.

The glycol material can comprise low molecular weight polyols, such as polyols having a molecular weight of less than 500, and compatible mixtures thereof. As used herein, the term "compatible" means that the glycols are mutually soluble in each other so as to form a single phase. Non-limiting examples of these polyols can include low molecular weight diols and triols. If used, the amount of triol is chosen so as to avoid a high degree of cross-linking in the polyurethane. A high degree of cross-linking can result in a curable polyurethane that is not formable by moderate heat and pressure. The organic glycol typically contains from 2 to 16, or from 2 to 6, or from 2 to 10 carbon atoms. Non-limiting examples of such glycols and other polyols can include ethylene glycol, propylene glycol, diethylene glycol, triethylene glycol, tetraethylene glycol, dipropylene glycol, tripropylene glycol, 1,2-, 1,3- and 1,4-butanediol, 2,2,4-trimethyl-1,3-pentanediol, 2-methyl-1,3-pentanediol, 1,3-2,4- and 1,5-pentanediol, 2,5- and 1,6-hexanediol, 2,4-heptanediol, 2-ethyl-1,3-hexanediol, 2,2-dimethyl-1,3-propanediol, 1,8-octanediol, 1,9-nonanediol, 1,10-decanediol, 1,4-cyclohexanediol, 1,4-cyclohexanedimethanol, 1,2-bis(hydroxyethyl)-cyclohexane, glycerin, tetramethylolmethane, such as but not limited to pentaerythritol, trimethylolethane and trimethylolpropane; and isomers thereof. Other suitable polyols for preparing polyurethane may be found in "Polyurethane Handbook", by Gunter Oertel and US 2017/0015805. Polyester polyols formed by the reaction of aliphatic or aromatic dicarboxylic acids with glycols can also be used as the polyol compound for preparing the polyurethane. Specific examples of acids for forming the polyester polyols include isophthalic terephthalic, and adipic acids.

In one embodiment, the present invention relates to polyurea thermosets prepared by the reaction of a compound containing at least two isocyanate groups, and an amine curing agent which comprises at least one compound selected from the Formulae (I) and (II):

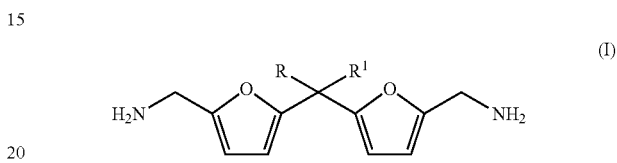

wherein (i) R is hydrogen and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

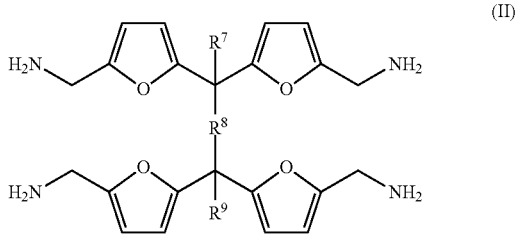

(II)

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to carbon atoms and an optionally substituted cycloalkylene group having 3 to 12 carbon atoms; and the alkylene group, the alkenylene group, the divalent heterocyclic group, the arylene group, and the cycloalkylene group of $R^8$ can be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

In another embodiment, the amine curing agent used to prepare the polyurea thermoset may be selected from any of the furan-containing compounds, as described herein. The compound containing two isocyanates may be selected from toluene diisocyanate, hexamethylene diisocyanate, isopheronediisocyanate, methylenediphenyldiisocyanate, 1,4-cyclohexane diisocyanate and a polyisocyanate oligomer.

Preferably, polyisocyanate oligomer is used as it capable of reducing inhalation hazards and reducing uptake through the skin.

Polymerization can be done around room temperature. No solvent or catalysts are needed.

In another aspect, the present disclosure relates to polyurea thermoplastics prepared by the reaction of a compound containing two isocyanate groups, and an amine curing agent which comprises at least one compound selected from the Formulae (I) and (II):

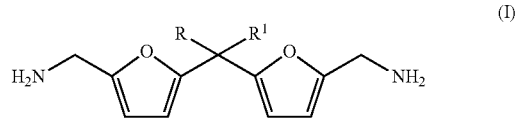

(I)

wherein (i) R is hydrogen and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and $R^1$ can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; and $R^1$ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of $R^1$ can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms;

Preferably, the amine monomer is selected form a diamine compound, as set forth above.

The compound containing two isocyanates may be selected from toluene diisocyanate, hexamethylene diisocyanate, isopheronediisocyanate, methylenediphenyldiisocyanate, and 1,4-cyclohexane diisocyanate.

Polymerization can be done around room temperature. Any organic solvent that solubilizes the monomers could be used, for example, chloroform, dichloromethane, and anhydrous acetone. Interfacial polymerization is typically not used because water reacts with isocyanates.

Preferably, the amines and solvents would be dried before polymerization to eliminate water and typically a purge gas is used, for example, $N_2$ or argon. Also, preferably, alcohol solvents are not used because they react with isocyanates.

Polyamide Thermoplastic

The polyamide thermoplastic of the present invention may be prepared by the reaction of a compound containing two carboxylic acid groups or two acyl chloride groups or acid chloride, methyl ester or $C_{2-12}$ alkyl esters thereof, and an amine curing agent which comprises at least one compound selected from the Formulae (I) and (II):

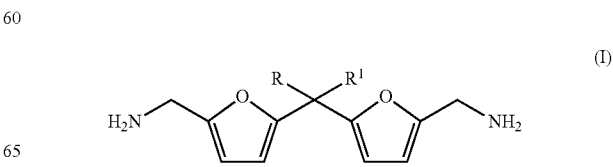

(I)

wherein (i) R is hydrogen and R¹ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and R¹ can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; and R¹ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R¹ can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms.

In a preferred embodiment, the amine monomer is selected from the diamine compounds set forth above.

Preferably, the compound containing two carboxylic acid groups or two acyl chloride groups or acid chloride, methyl ester or $C_{2-12}$ alkyl esters thereof, is selected from oxalic acid, terephthalic acid, phthalic acid, furandicarboxylic acid, and 1,6-napthylenedicarboxylic acid.

The polyamide thermoplastic can be made by interfacial polymerization or a bulk solution method.

Interfacial Polymerization

Interfacial polymerization is described in the literature [12-16]. Polyamides are prepared through interfacial polymerization in a three-neck, 100-mL round-bottom flask equipped with a mechanical stirrer, and $N_2$ gas inlet. Diamines (2-5 g), 5 wt-% tetrabutylammonium bromide (TBAB) catalyst (0.25-0.5 g), and 0.15-0.20 M NaOH solution (15-20 mL) are added to the flask and stirred at RT under nitrogen until all components are completely dissolved. The dicarboxylic acid chloride (4-6 g—stoichiometric amount) is dissolved in chloroform (15-20 mL) and added in aliquots to the stirring diamine solution. Evolution of HCl gas forms upon addition and continues until several minutes after all acid chloride solution is added. The reaction is allowed to stir for 2 h. The solid polymer is filtered and thoroughly washed with water (200 mL) and acetone (100 mL). The polymer is then dissolved in DMSO solvent and stirred overnight. The solution is filtered to remove any insoluble material and the solution is precipitated into water (500 mL). The biobased furan polyamide is filtered and dried under vacuum at 105-120° C.

Bulk Solution Method

The polyamides can be prepared by a bulk solution method according to the literature using "direct" polycondensation using a Yamazaki-Higashi phosphorylation reaction.(17-19) Polyamides are prepared in a three-neck, 100-ml round-bottom flask equipped with a mechanical stirrer, and gas inlet. 2,5-Furan dicarboxylic acid (2.00 g, 12.8 mmol), p-phenylene diamine (1.42 g, 13.1 mmol), LiCl (0.55 g, 12.9 mmol), N-Methyl-2-pyrrolidone (NMP) (10 mL), and pyridine (7 mL), as a azeotroping agent was added to the flask. The mixture is stirred for 25-30 min at 100° C., and then the temperature is ramped to 110° C. After 1 hour, the temperature is ramped again to 140° C. and the catalyst, triphenyl phosite (6.4 mL), is added to the mixture. After addition of the catalyst, the reaction rapidly changes from a medium brown to a dark green color. The reaction temperature is ramped twice more to achieve a final temperature of 185° C. and is allowed to soak overnight at that temperature. The reaction contents are precipitated into aqueous HCl solution dropwise forming dark green to brown solids. The material is filtered and washed with methanol (50-mL, 3×). The product is dried in an oven at 80-90° C. overnight under reduced pressure.

Thermoset and Thermoplastic Michael Addition Product

In one embodiment, the thermoplastic Michael addition products may be prepared by the reaction of: a compound containing two methacrylate and/or acrylate groups, and an amine curing agent which comprises at least one compound selected from the Formulae (I):

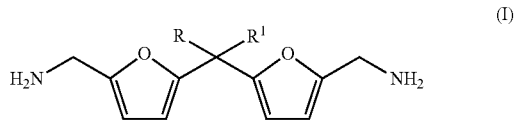

(I)

wherein (i) R is hydrogen and R¹ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and R¹ can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms; and R¹ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R¹ can be substituted with 1 to 5 substituents independently selected from halogen, hydroxy, nitro, cyano, carboxy, an alkyl group having 1 to 20 carbons, a heterocyclic group having 3 to 16 carbons, and an alkoxy group having 1 to 20 carbon atoms.

In a preferred embodiment, the amine monomer is selected from a diamine compound.

In another embodiment, the thermoset Michael addition product prepared by the reaction of:
a compound containing at least two methacrylate and/or acrylate groups, and
an amine curing agent which comprises at least one compound selected from the Formulae (I): and (II):

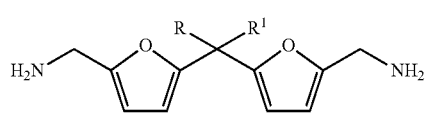

(I)

wherein (i) R is hydrogen and R¹ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R and R¹ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; or (ii) R is selected from an optionally substituted alkyl group having 1 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and R¹ is selected from an optionally substituted alkyl group having 2 to 20 carbon atoms, an optionally substituted alkene group having 2 to 20 carbon atoms, an optionally substituted cycloalkyl group having 3 to 12 carbon atoms, an optionally substituted aryl group having 6 to 16 carbon atoms, and an optionally substituted heterocyclic group having 3 to 16 carbon atoms; and the alkyl group, the alkene group, the cycloalkyl group, the aryl group and the heterocyclic group of R¹ can be substituted with 1 to 5 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms; and

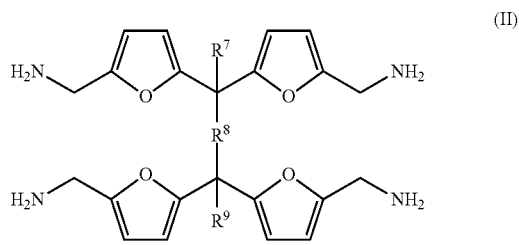

(II)

wherein $R^7$ and $R^9$ are independently selected from hydrogen, an optionally substituted alkyl group having 1 to 20 carbon atoms, an optionally substituted alkene group having 2 to 20 carbon atoms, an optionally substituted heterocyclic group with 3 to 15 carbon atoms, an optionally substituted aryl group having 6 to 15 carbon atoms and an optionally substituted cycloalkyl group having 3 to 12 carbon atoms; the alkyl group, the alkene group, the heterocyclic group, the aryl group, and the cycloalkyl group can be substituted with 1 to 5 substituents independently selected from halogen, hydroxy, amino, nitro, cyano, carboxy, an alkyl group having 1 to 20 carbons, an aryl group having 6 to 15 carbon atoms, a heterocyclic group having 3 to 16 carbons, and an alkoxy group having 1 to 20 carbon atoms, and wherein the aryl group substituent and the heterocyclic group substituent can be further substituted with hydroxy, an alkoxy group having 1 to 20 carbon atoms, or an alkylamino group having 1 to 2 carbon atoms; and $R^8$ is an optionally substituted alkylene group having 1 to 20 carbon atoms, an optionally substituted alkenylene group having 2 to 20 carbon atoms, an optionally substituted divalent heterocyclic group with 3 to 15 carbon atoms, an optionally substituted arylene group having 6 to 15 carbon atoms and an optionally substituted cycloalkylene group having 3 to 12 carbon atoms; and the alkylene group, the alkenylene group, the divalent heterocyclic group, the arylene group, and the cycloalkylene group of $R^8$ can be substituted with 1 to 4 substituents independently selected from halogen, hydroxy, amino, nitro, cyano, carboxy, an alkyl group having 1 to 20 carbons, a heterocyclic group having 3 to 16 carbons, and an alkoxy group having 1 to 20 carbon atoms.

EXAMPLES

The following examples are illustrative, but not limiting, of the methods and compositions of the present disclosure.

The following materials were employed throughout the examples: Furfurylamine (99%), hydrochloric acid (37%), chloroform, vanillin (99%), syringaldehyde (98%), terephthalaldehyde (99%), cuminaldehyde (98%), p-tolualdehyde (97%), cyclohexanecarboxaldehyde (97%), octanal (98%), sodium hydroxide (98%) and tetrahydrofuran (THF, 99.9%) were supplied by Sigma-Aldrich, USA; diglycidyl ether of bisphenol A (DGEBA, n=0.13) (Momentive EPON Resin 828) was obtained from Miller-Stephenson chemicals and Air Products, USA, respectively. All chemicals were used as received. The following schematic is a general reaction scheme for furan based amines.

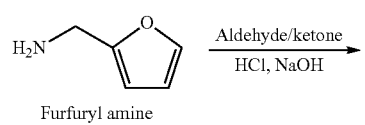
Furfuryl amine
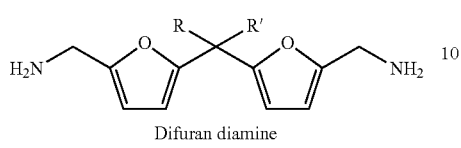
Difuran diamine
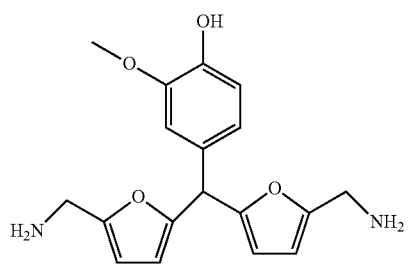
1
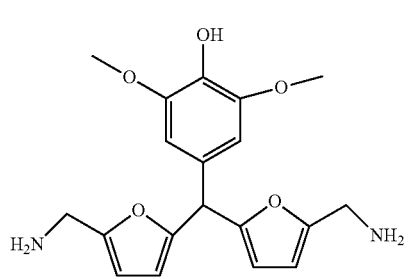
2
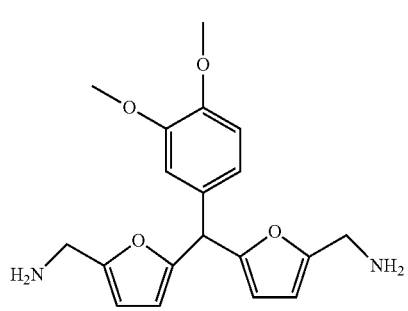
3
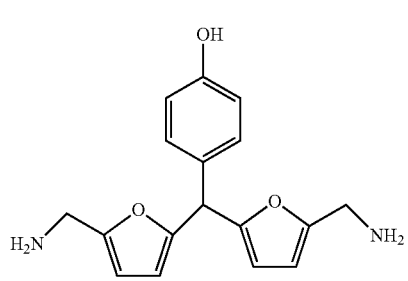
4
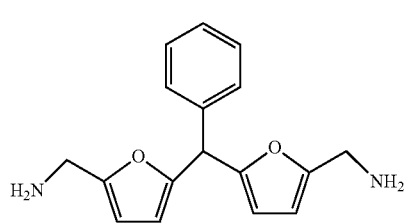
5
-continued
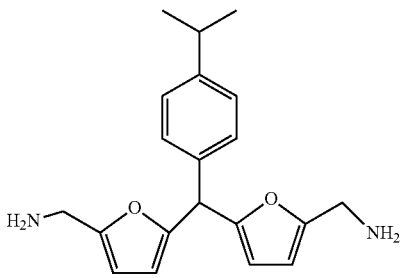
6
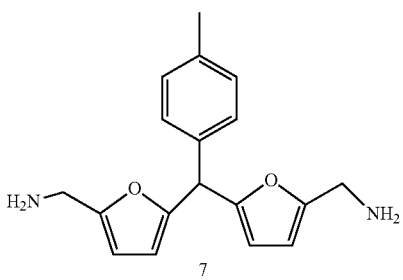
7
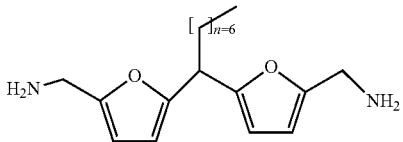
8
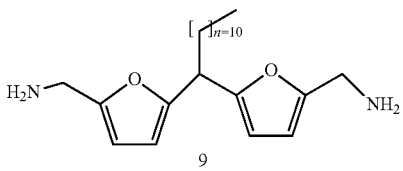
9
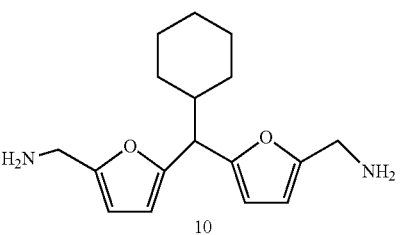
10
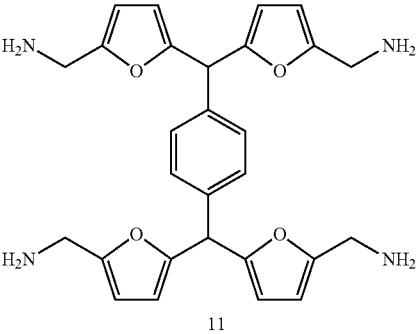
11

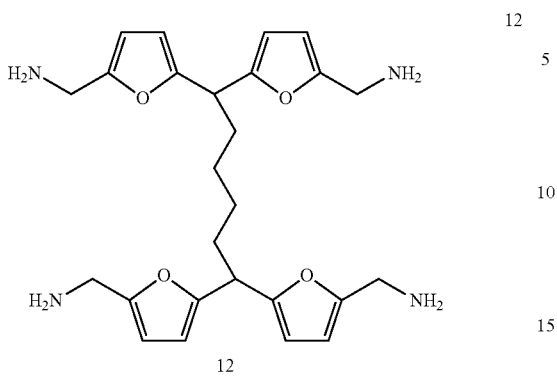

12

Chemical Structures of Various Furan Based Amines Used in the Examples

TABLE 1

Nomenclature of furan based amines and used bridging aldehydes for the synthesis.

| Number* | Furan based amines | General Name | Bridging Aldehydes |
|---|---|---|---|
| 1 | 4-{bis[5-(aminomethyl)furan-2-yl]methyl}-2-methoxyphenol | V-DFDA | Vanillin |
| 2 | 4-{bis[5-(aminomethyl)furan-2-yl]methyl}-2,6-dimethoxyphenol | Syringal-DFDA | Syringaldehyde |
| 3 | {[(3,4-dimethoxyphenyl)methanediyl]difuran-5,2-diyl}dimethanamine | Dimethoxy benzyl-DFDA | 3,4-Dimethoxybenzaldehyde |
| 4 | 4-{bis[5-(aminomethyl)furan-2-yl]methyl{phenol | Methoxy-benzyl-DFDA | 4-Hydroxybenzaldehyde |
| 5 | [(phenylmethanediyl)difuran-5,2-diyl]dimethanamine | Benyl-DFDA | Benzaldehyde |
| 6 | {[(4-methylphenyl)methanediyl]difuran-5,2-diyl}dimethanamine | p-tlual-DFDA | p-Tolualdehyde |
| 7 | ({[4-(propan-2-yl)phenyl]methanediyl}difuran-5,2-diyl)dimethanamine | Cumin-DFDA | Cuminaldehyde |
| 8 | [(cyclohexylmethanediyl)difuran-5,2-diyl]dimethanamine | Cyclohex-DFDA | Cyclohexane-carboxaldehyde |
| 9 | (octane-1,1-diyldifuran-5,2-diyl)dimethanamine | Oct-DFDA | Octanal |
| 10 | (dodecane-1,1-diyldifuran-5,2-diyl)dimethanamine | Laural-DFDA | Lauraldehyde |
| 11 | (5,5',5'',5'''-(1,4-phenylenebis(methanetriyl))tetrakis(furan-5,2-diyl))tetramethanamine | TFTA | Terephthaldehyde |
| 12 | (5,5',5'',5'''-(pentane-1,1,5,5-tetrayl)tetrakis(furan-5,2-diyl))tetramethanamine | Glutaral-TFTA | Glutaraldehyde |

*Number corresponds to chemical structures disclosed in previous page.

List of other Bridging Aldehydes

4-Tertbutyl benzaldehyde, 4-Ethyl benzaldehyde, 4-propyl benzaldehyde, 4-butyl benzaldehyde, 4-pentyl benzaldehyde, 4-hexyl benzaldehyde, 4-octyl benzaldehyde, 4-ethoxybenzaldehyde, 4-Butoxybenzaldehyde etc.

Synthesis of Furan Based Amines

TABLE 2

Summary of reaction conditions for furan based amines.

| Amines | Aldehydes | Amine/Aldehyde ratio | React. Temp | React. Time | Purity ($^1$H-NMR) | Yield |
|---|---|---|---|---|---|---|
| V-DFDA | Vanillin | 1:10 | 40° C. | 24 h | 99% | 76% |
| Syring-DFDA | Syringaldehyde | 1:10 | 40° C. | 48 h | 97% | 42% |
| B-DFDA | Benzaldehyde | 1:10 | 40° C. | 24 h | 99% | 73% |
| Cumin-DFDA | Cuminaldehyde | 1:10 | 40° C. | 24 h | 99% | 38% |

TABLE 2-continued

Summary of reaction conditions for furan based amines.

| Amines | Aldehydes | Amine/Aldehyde ratio | React. Temp | React. Time | Purity ($^1$H-NMR) | Yield |
|---|---|---|---|---|---|---|
| Cyclohex-DFDA | Cyclohexanecarboxaldehyde | 1:10 | 40° C. | 24 | 88% | 34% |
| OCT-DFDA | Octanal | 1:10 | 40° | 24 | 99% | 12% |
| LAU-DFDA | Lauraldehyde | 1:10 | 40° | 24 | 99% | 6% |
| TFTA | Terephthalaldehyde | 1:20 | 40° C. | 24 h | 99% | 78% |

4-{bis[5-(aminomethyl)furan-2-yl]methyl}-2-methoxyphenol (V-DFDA) (1)

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and vanillin 7.05 g (46.3 mmol) was added to the reaction mixture. The reaction was carried out at 40° C. for 24 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. The 76% yield of 4-{bis[5-(aminomethyl)furan-2-yl]methyl}-2-methoxyphenol was obtained after distillation and purification with a 99% purity determined by $^1$H NMR (FIG. 3) (CDCl$_3$, 500 MHz, ppm): δ 3.76 (s, 4H), 3.83 (s, 3H) 5.31 (s, 1H), 5.88 (d, furanic 2H), 6.03 (d, furanic 2H), 6.68-6.86 (m, 3H).

4-{bis[5-(aminomethyl)furan-2-yl]methyl}-2,6-dimethoxyphenol (Syringal-DFDA) (2)

Figure 4:
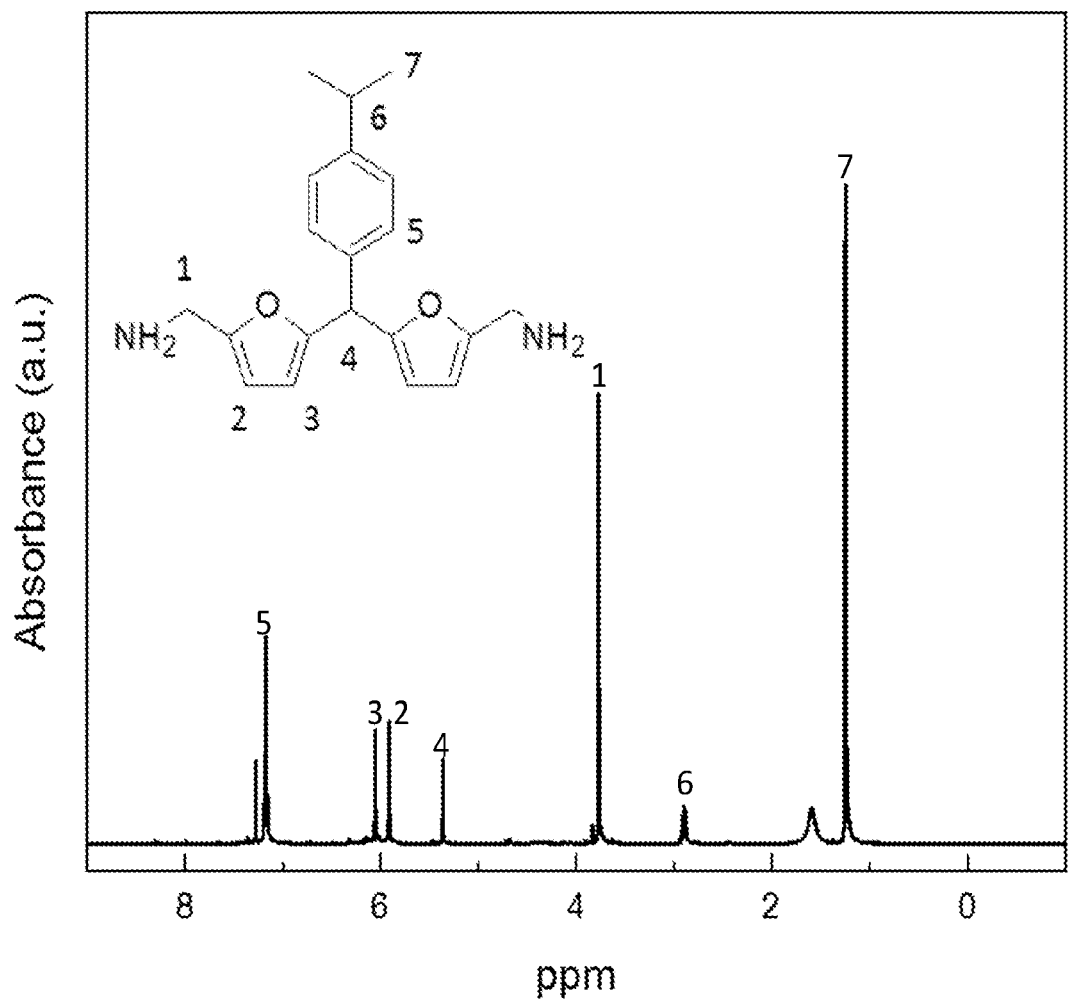
FIG. 4 shows the $^1$H NMR spectra of ({[4-(propan-2-yl)phenyl]methanediyl}difuran-5,2-diyl)dimethanamine (Cumin-DFDA).
Figure 5:
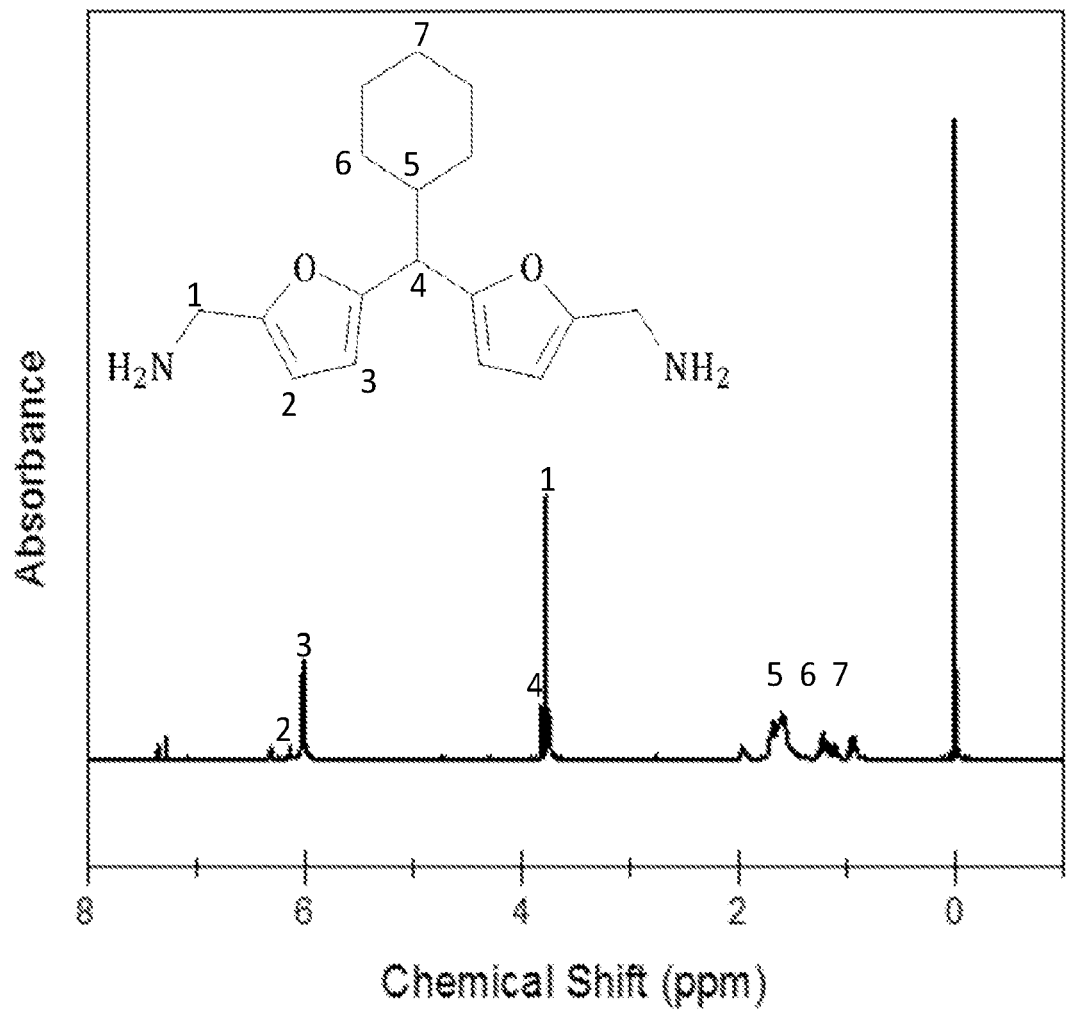
FIG. 5 shows the $^1$H NMR spectra of [(cyclohexylmethanediyl)difuran-5,2-diyl]dimethanamine (Cyclohex-DFDA).

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and syringaldehyde 8.43 g (46.3 mmol) was added to the reaction mixture. The reaction was carried out at 40° C. for 48 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. The 45% yield of bis[5-(aminomethyl)furan-2-yl]methyl}-2,6-dimethoxyphenol was obtained after distillation and purification with a 97% purity determined by $^1$H-NMR (FIG. 4). by $^1$H NMR (CDCl$_3$, 500 MHz, ppm): δ 3.77 (s, 4H), 3.82 (s, 3H), 5.29 (s, 1H), 5.9 (d, furanic, 2H), 6.06 (d, furanic 2H), 6.46 (s, 3H).

[(phenylmethanediyl)difuran-5,2-diyl]dimethanamine] (Benzyl-DFDA). (5)

Figure 3:
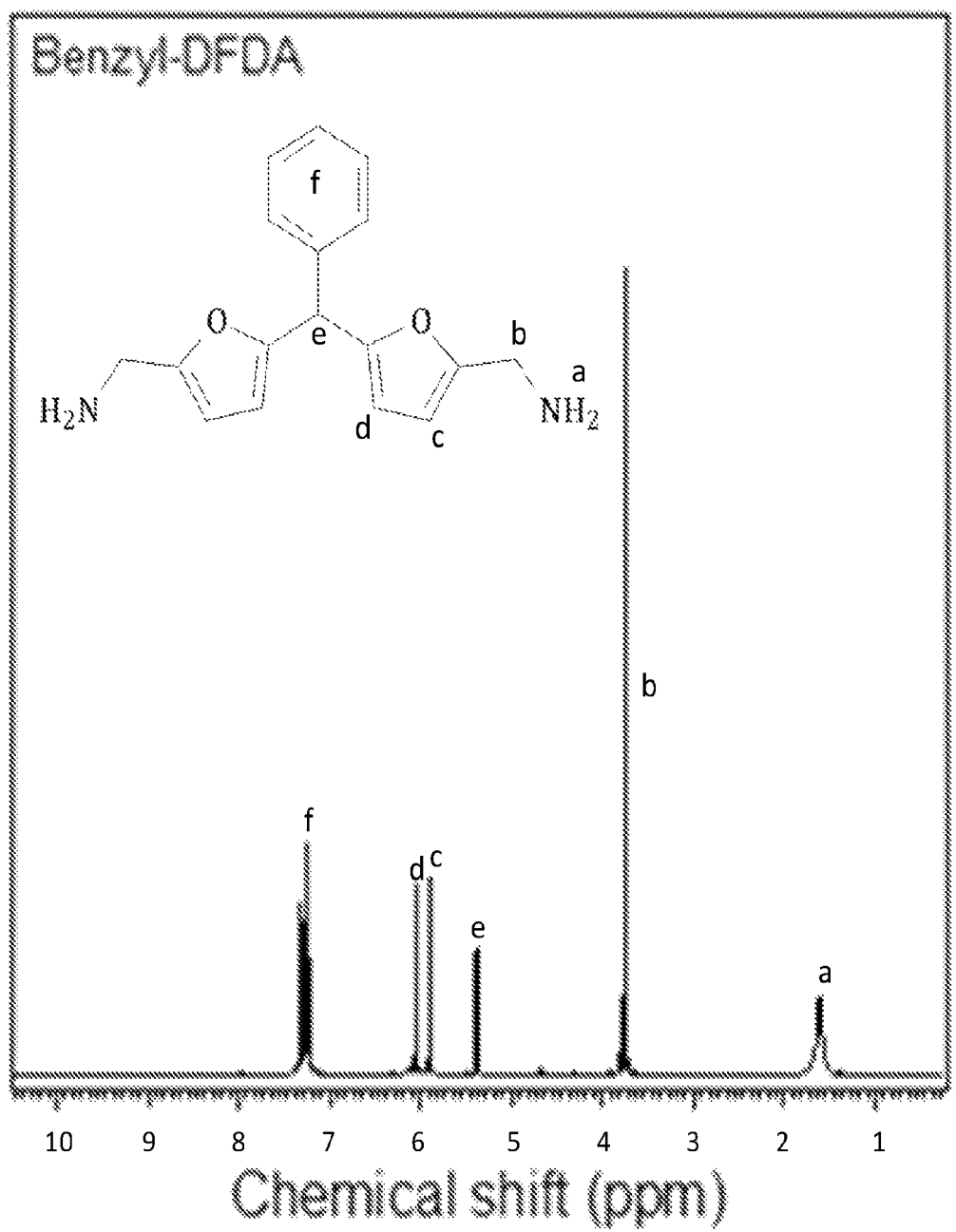
FIG. 3 shows the $^1$H NMR spectra of [(phenylmethanediyl)difuran-5,2-diyl]dimethanamine] (Benzyl-DFDA).

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and benzaldehyde 4.92 g (46.3 mmol) was added to the reaction mixture. The reaction was carried out at 25° C. for 24 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. The 42% yield of [(phenylmethanediyl)difuran-5,2-diyl]dimethanamine was obtained after distillation and purification with a 97% purity determined by $^1$H-NMR (FIG. 3). $^1$H NMR (CDCl$_3$, 500 MHz, ppm): δ 3.77 (s, 4H), 5.4 (s, 1H), 5.85 (d, furanicHz, 2H), 6.08 (d, furanic 2H), 7.2-7.4 (m, 5H).

({[4-(propan-2-yl)phenyl]methanediyl}difuran-5,2-diyl)dimethanamine(Cumin-DFDA) (7)

Figure 6:
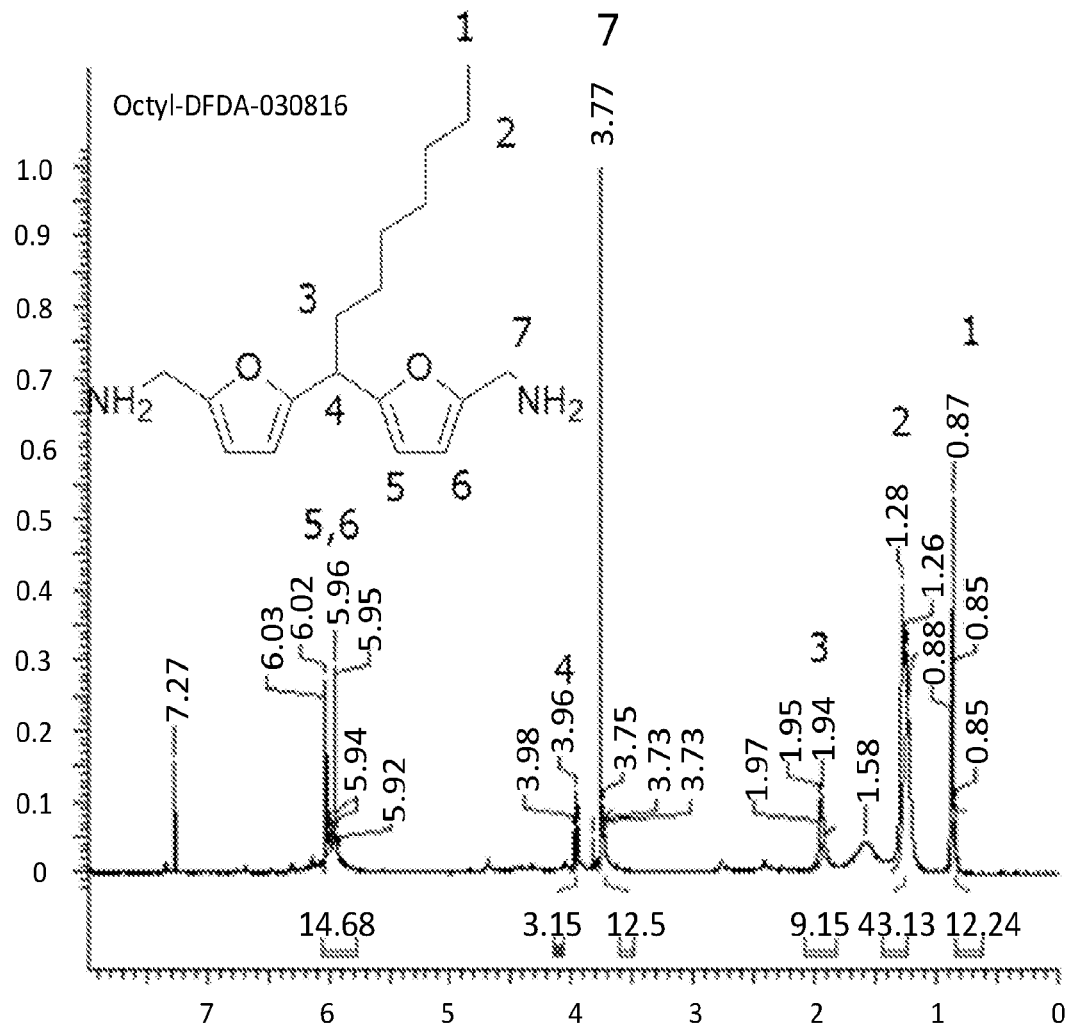
FIG. 6 shows the $^1$H NMR spectra of (octane-1,1-diyldifuran-5,2-diyl)dimethanamine (OCT-DFDA).

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and cuminaldehyde 6.86 g (46.3 mmol) was added to the reaction mixture. The reaction was carried out at 40° C. for 24 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. A 38% yield was obtained after distillation and purification with a 99% purity determined by $^1$H NMR (FIG. 6).

[(cyclohexylmethanediyl)difuran-5,2-diyl]dimethanamine (Cyclohex-DFDA) (8)

Figure 7:
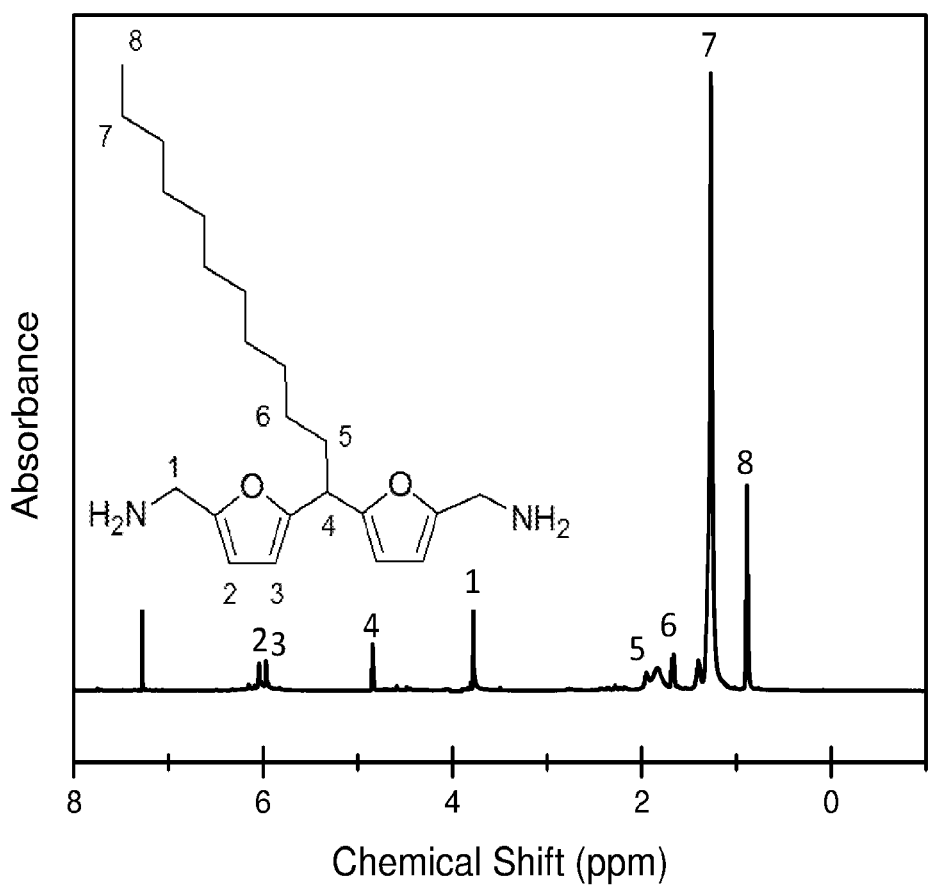
FIG. 7 shows the $^1$H NMR spectra of (dodecane-1,1-diyldifuran-5,2-diyl)dimethanamine (LAU-DFDA).

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and Cyclohexanecarboxaldehyde 5.19 g (46.3 mmol) was added to the reaction mixture. The reaction was carried out at 40° C. for 24 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. A 34% yield was obtained after distillation and purification with a 88% purity determined $^1$H NMR (FIG. 7).

(octane-1,1-diyldifuran-5,2-diyl)dimethanamine (OCT-DFDA) (9)

Figure 8:
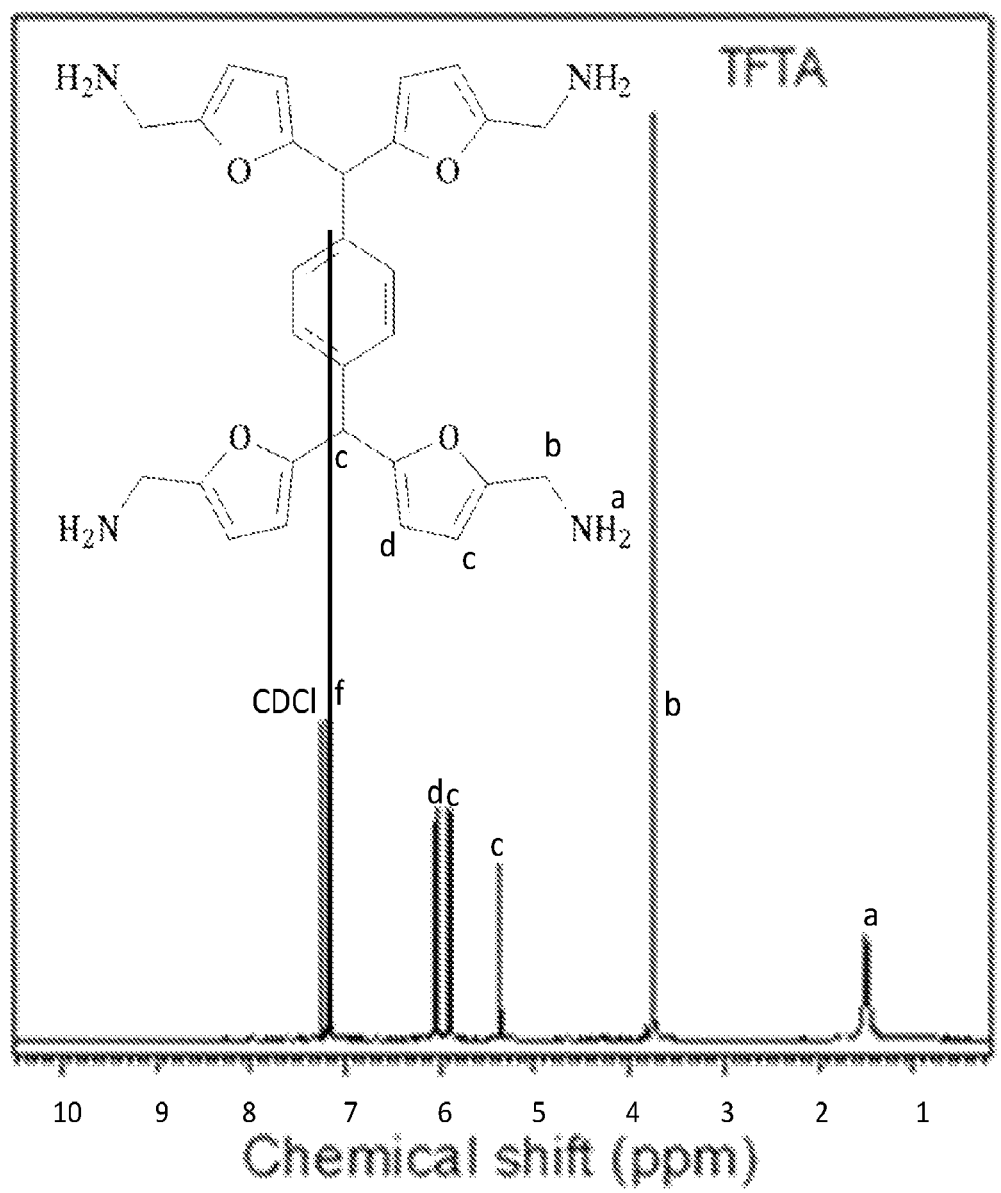
FIG. 8 shows the $^1$H NMR spectra of (5,5',5'',5'''-(1,4-phenylenebis(methanetriyl))tetrakis (furan-5,2-diyl))tetramethanamine (TFTA).

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and octanal 5.93 g (46.3 mmol) was added to the reaction mixture. The reaction was carried out at 40° C. for 24 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. The 12% yield was obtained after distillation and purification with a 99% purity determined by $^1$H NMR (FIG. 8).

(dodecane-1,1-diyldifuran-5,2-diyl)dimethanamine (LAU-DFDA) (10)

Figure 9:
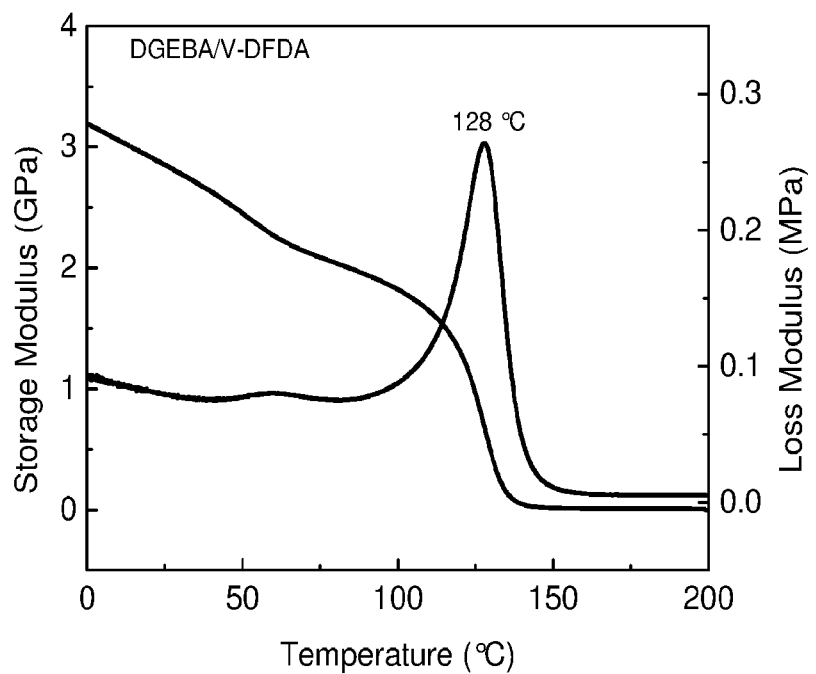
FIG. 9 shows Dynamic Mechanical Analysis (DMA) thermograms of cured samples of DGEBA with V-DFDA.

Furfurylamine (45 g, 463 mmol) was added to a 1000 mL round-bottom flask and cooled in an ice bath to 25° C. 6 M hydrochloric acid (330 mL, 2 mol) was added slowly, using the ice bath to maintain the temperature at or near 25° C. The reaction flask was removed from the ice bath, and octanal 8.53 g (46.3 mmol) was added to the reaction mixture. The reaction was carried out at 40° C. for 24 h. After completion of the reaction, the mixture was neutralized by the addition of 6 M sodium hydroxide (330 mL, 2 mol) and extracted with chloroform (2×110 mL). The combined chloroform layers were washed with distilled water (100 mL), dried over anhydrous MgSO$_4$ and evaporated to yield the final product. The 6% yield was obtained after distillation and purification with a 99% purity determined by $^1$H NMR (FIG. 9).

(5,5',5'',5'''-(1,4-phenylenebis(methanetriyl))tetrakis (furan-5,2-diyl))tetramethanamine (TFTA) (11)

Figure 10:
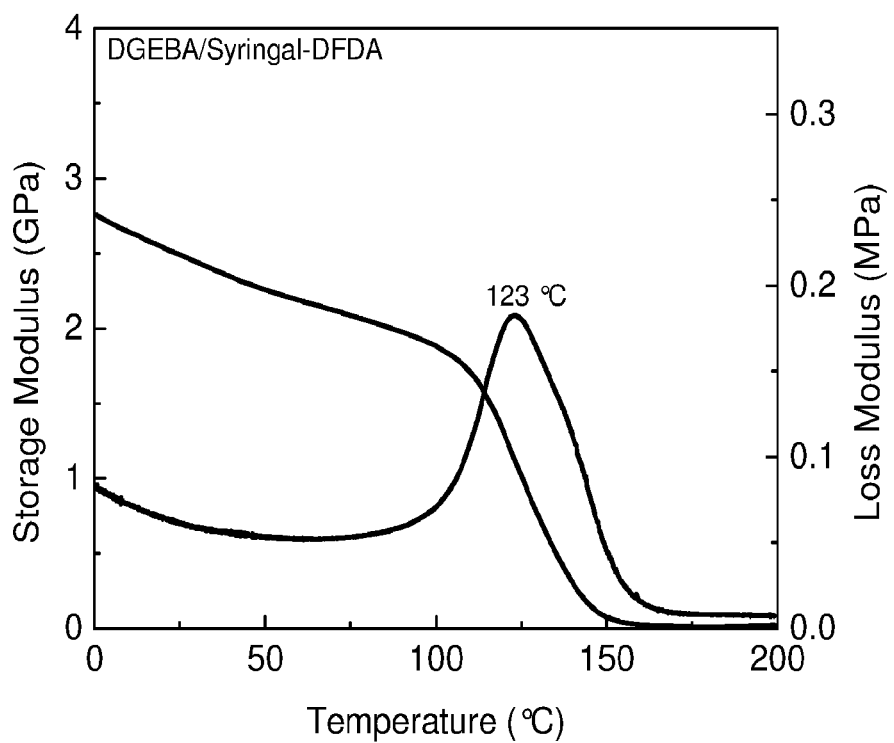
FIG. 10 shows Dynamic Mechanical Analysis (DMA) thermograms of cured samples of DGEBA with Syringal-DFDA.
Figure 11:
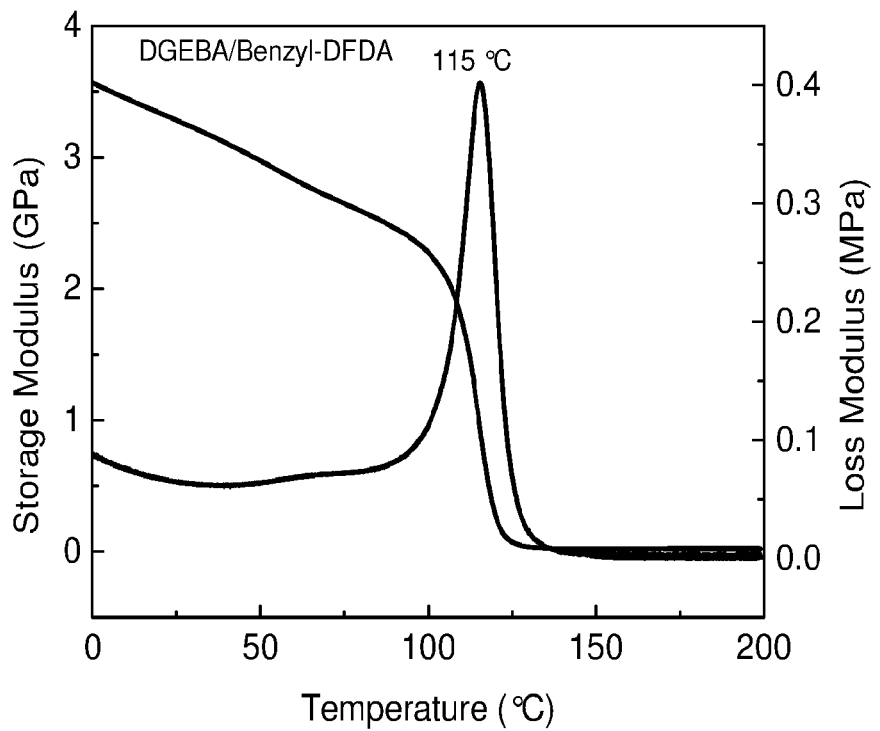
FIG. 11 shows Dynamic Mechanical Analysis (DMA) thermograms of cured samples of DGEBA with Benzyl-DFDA.
Figure 12:
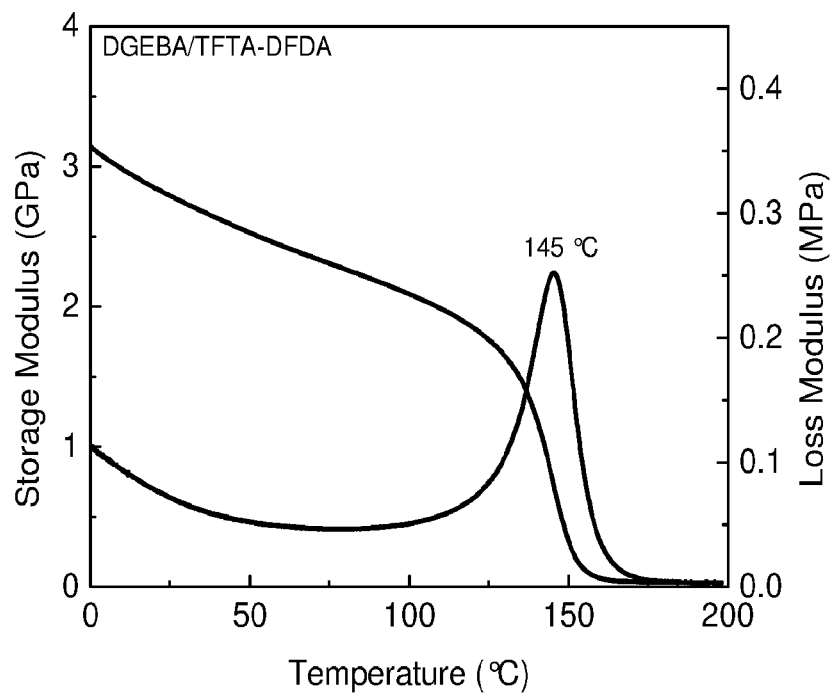
FIG. 12 shows Dynamic Mechanical Analysis (DMA) thermograms of cured samples of DGEBA with TFTA.

Furfurylamine (50 g, 515 mmol) and 6 M HCl solution (330 mL, 2 mol) were combined in a round-bottom flask. This solution was brought to 40° C., and terephthalaldehyde (3.76 g, 25.7 mmol) was added to the solution. After 24 h, the reaction mixture was cooled in an ice bath and neutralized with a solution of 6 M sodium hydroxide (330 mL, 2 mol). The product was recovered by extraction with chloroform (2×100 mL). The combined extract was washed with water. The final solution is dried on magnesium sulfate overnight and rotary evaporated. The unreacted furfurylamine was removed by vacuum distillation and yielded a brown solid (yield: 78%) with 99% purity determined by $^1$H-NMR (FIG. 10). $^1$H NMR (CDCl$_3$, 500 MHz, ppm): δ 1.5 (s, 8H), 3.76 (s, 8H), 5.38 (s, 2H), 5.9 (d, furanic 4H), 6.03 (d, furanic 4H), 7.16 (s, 4H).

Preparation of Epoxy-Amine Thermoset Polymers

A series of epoxy-amine thermosetting resins was prepared with the aim of elucidating their structure-property relationships. The mass ratio for mixing was determined using the epoxy equivalent weight (EEW) and amine hydrogen equivalent weight (AHEW. To obtain a thermosetting network, all furan based di and tetra amines were cured with DGEBA at stoichiometric amounts. Epoxy monomers and amine hardeners were mixed in stoichiometric amounts, i.e. two epoxy groups to one amine. This theoretical ratio has been proven to result in materials with the best properties. V-DFDA, Syringal-DFDA and TFTA are solid monomers. DGEBA/Syringal-DFDA, DGEBA/V-DFDA and DGEBA/TFTA were prepared from pre-heated monomers at 120° C. in the liquid state in order to avoid any macro-defect such as air bubbles.

V-DFDA, Syringal—DFDA and TFTA are solid monomers so epoxy/amine samples can also be prepared with solvent to improve processability by decreasing the solution viscosity. In the processing studies, the epoxy-amine solutions contained DGEBA epoxy component and furan based amines curing agent mixed in the same ratio as the neat samples with tetrahydrofuran (THF) comprising 40% of the mixture by mass. The amine hardener-epoxy resin combinations were mixed and cast on glass plate. Higher temperatures were required to process the samples to remove solvent during cure. The samples were cured at 80° C. under vacuum for 12 hours and post-cured at 180° C. for 12 hours.

Material Characterization

Proton Nuclear Magnetic Resonance ($^1$H NMR)

$^1$H-NMR spectroscopy was used to verify the chemical structure and purity of synthesized epoxy monomer and furan based diamines. A $^1$H NMR (500 MHz, Varian Unity Inova) unit was used to confirm the chemical structures of furan based amines with a spectral window of ±2000 Hz, 90° pulse width and 16 scans at 25° C.

Fourier Transform Infrared Spectroscopy

To verify the full conversion of epoxy and amine groups, FTIR in the near-infrared region (4000-8000 cm$^{-1}$) was used. A NIR Spectrometer Nicolet 6700 with a CaF$_2$ beam splitter was employed for this purpose. NIR spectra were collected at a resolution 8 cm$^{-1}$ resolution with 34 scans, transmission mode. The peaks involved are the epoxy peak at 4530 cm$^{-1}$, the primary amine peak at 4925 cm-1, and the primary/secondary amine peak at 6510 cm$^{-1}$.

Density

The density for all samples were measured via a density gradient column as described in ASTM D1505. All specimens were thin films with an average thickness of 100 m; these films were immersed in DI water at 23° C. for about 10 min prior to exposure to the density gradient to ensure no air bubbles would form. The density of each composition was taken to be the average of at least three representative samples from a film of desired composition.

Dynamic Mechanical Analysis (DMA)

The samples were prepared uniform dimensions, 17.5 mm×12 mm×2.9 mm. The thermomechanical properties of a single sample of each of the cured resins were probed using a TA Instruments Q800 DMA. Samples were run at a 1.0 Hz frequency, a set Poisson's ratio of 0.35, and a deflection amplitude of oscillation of 7.5 μm with a heating ramp of 2° C. min$^{-1}$ from 0.0° C. to 200° C. The T$_g$ of each sample was taken to be the peak of the loss modulus (E") curve.

Water Sorption

Water barrier properties of model amido amines cured with DGEBA were measured using a TA model Q5000SA Dynamic Vapor Sorption device. Each sample was dried in situ at 85° C. and at 0% RH before exposure to humidity to ensure fully dry samples before testing. Each composition was exposed to 80% RH at 24, 36, 48, and 60° C.

For one-dimensional diffusion through a slab with thickness L, Fick's second law with a constant diffusion coefficient or diffusivity, D, is given in Equation 3 where C is the moisture concentration and t is time.

$$\frac{\partial C}{\partial t} = D\frac{\partial^2 C}{\partial x^2} \quad (1)$$

The diffusion of water into glassy polymers generally exhibits Fickian behavior when the transport of water is completely controlled by diffusion, that is, when diffusion mechanisms related to degradation, segmental relaxation, or insufficient curing, for example are not active.[3,4] Assuming a symmetrical slab geometry with a surface concentration equal to the solution concentration, the integrated form of the analytical solution to Fick's Second Law is given by Equation 4

$$\frac{M(t)}{M_{eq}} = 1 - \sum_{n=0}^{\infty} \frac{8}{(2n+1)^2\pi^2}\exp\left(\frac{-D(2n+1)^2\pi^2}{4L^2}\right) \quad (2)$$

Where M(t) is the mass of the sample at any time (t) and $M_{eq}$ is the mass the sample reaches at saturation. Characteristic features of Fickian diffusion are: an initially linear plot of M(t) vs $t^{1/2}$, and that the absorption curve smoothly levels off to a saturation level $M_{eq}$.[5] However in some cases, it is beneficial to weigh the initial sorption data more heavily than the late time water uptake data to obtain better fits for D. In these cases for an initially dry material, the value D can be calculated form the initial slope of a plot of M(t) as a function of $t^{1/2}/L$ using the Equation 5.[6]

$$\frac{M(t)}{M_{eq}} = \frac{4}{l}\sqrt{\frac{Dt}{\pi}} \rightarrow D = \left(\frac{M(t)}{\sqrt{t}}\right)^2 \frac{\pi l^2}{16 M_{eq}}. \quad (3)$$

Epoxy Cured with Furan Based Amines

To obtain thermosetting network, furan based di and tetra amines were cured with DGEBA epoxy at stoichiometry. This theoretical ratio has been proven to give the materials with the best properties. Full conversion of epoxy and amine groups in polymer samples was verified using a Thermo Nicolet Nexus 870 N-IR spectrometer. Spectra of postcured samples were recorded in a range of 4000-8000 cm$^{-1}$ with 8 cm$^{-1}$ resolution and 32 scans operated in absorbance mode at RT. Spectra of the neat monomers and the cured samples were taken using a Nicolet *Nexus* 870 infrared spectrometer. The spectra of the cured samples were qualitatively examined for residual epoxy or amine functionality NIR spectra of cured. After curing, the oxirane and amine signals are observed to decrease (due to chemical reaction with each other), while a broad hydroxyl absorption around 6500-7000 cm$^{-1}$ is seen to increase as residual hydroxyl groups are formed during curing. The oxirane absorption at 4530 cm$^{-1}$ was used to quantify the extent of cure and peaks ca. 6000 cm$^{-1}$ was used as internal references. Within the limits of n-IR spectrometry, all resins were >99% cured with respect to the epoxy functionality.

Polymer Properties

Thermomechanical Properties

The furan based amine curing agents in this work were chosen in order to elucidate any structure-property relationships that may exist in these new furan based amine systems. DMA analyses of the samples were performed to investigate their thermo-mechanical properties of the polymer. Storage moduli E', and loss modulus E'' of each polymer are shown in FIGS. 9-12. The Tg determined at the maximum of the loss modulus curves.

To evaluate the impact DFDA derivatives on the properties of thermosetting network the commercially available DGEBA was cured with V-DFDA, Benzyl-DFDA, Cumin-DFDA and TFTA. The DMA results are summarized in FIG. 10. All samples show sharp loss modulus peaks, indicating their cured networks are homogeneous.

The sample DGEBA cured with V-DFDA had the higher Tg (Loss Modulus Tg 128° C.) compared to the other furan based amines cured samples DGEBA/Benzyl-DFDA (Tg 115° C.) and DGEBA/Cumin-DFDA (Tg 113° C.). The V-DFDA hardener showed the higher Tg with DGEBA epoxy polymer bears aromatic linkage and other functional groups (hydroxyl and methoxy groups) that confer rigidity to the network. The higher $T_g$ (145° C.) of the TFTA cured resins tetra functional amine compared to the furan based di amines is likely explained by a combination of factors regarding molecular structures. TFTA is tetra-functional, which results in a high cross-linking density. It also has the benzene ring in the core which makes more rigid structure than other DFDA derivatives.

To determine the effect of the aliphatic and aromatic substitutions of the amine monomers on the hydrophobicity of the resulting networks, the moisture uptakes of the epoxy-amine networks were measured (Table 1). DGEBA/Benzyl-DFDA and DGEBA/Cumin-DFDA adsorbed almost same amount of water 2.15% by mass, which is fairly lower value. However DGEBA/TFTA showed higher water uptake (2.53%). Further, furan based di amines with aliphatic chains networks showed significantly lower water uptake values.

TABLE 3

Properties of furan based amines cured DGEBA epoxy samples.

| Sample Code | Loss Modulus Tg (° C.) | Storage Modulus (GPa) at 25° C. | Density (g/cm$^3$) | Water uptake (wt %) |
|---|---|---|---|---|
| DGEBA/V-DFDA | 128 | 2.85 | 1.2276 | ND |
| DGEBA/Syring-DFDA | 123 | 2.5 | ND | ND |
| DGEBA/Benzyl-DFDA | 115 | 3.08 | 1.199 | 2.15 |
| DGEBA/CUMIN-DFDA | 113 | 2.98 | 1.185 | 2.14 |
| DGEBA/TFTA | 145 | 2.87 | 1.207655 | 2.53 |

ND = not measured

Preparation and Characterization of DFDA Tetra Epoxy (TGEDFDA)

A 1000 mL three-necked round-bottom flask equipped with a constant-pressure dropping funnel, a thermometer, a condenser and a magnetic stirring bar was used for the reaction. DFDA (40 g), epichlorohydrin (538.9 g) and tetra-butylammonium hydrogen sulfate (3.296 g) were charged into the flask with continuous stirring. The reaction was carried out for four hours at 80° C. Then the system was cooled in an ice bath. NaOH solution was charged into the constant-pressure dropping funnel and was added to the reaction vessel drop-wise. The reaction was continued at 30° C. for two hours. Three extractions were performed using ethyl acetate. The organic layer was collected and washed with brine several times and then dried using magnesium sulfate. A rotary evaporator was used to remove the ethyl acetate, leaving a dark brown viscous liquid. The epoxy resin was purified by flash chromatography to remove the impurities, which were mostly unreacted epichlorohydrin. The purity of the resulting resin was found to be 97% based on $^1$H NMR and epoxy equivalent weight titration.

The following schematic shows the reaction scheme for preparing the difuran diamine tetra epoxy (TGEDFDA):

Preparation of the Polymer

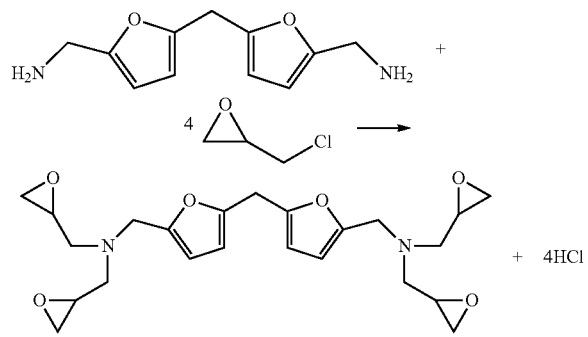

PACM and DFDA were used as curing agents in order to evaluate the thermal and mechanical properties of thermosets prepared with TGEDFDA. The chemical structures of TGEDFDA, PACM, and DFDA are given below. The epoxy equivalent weight (EEW) of TGEDFDA obtained experimentally was 107/eq. The amine hydrogen equivalent weight (AHEW) of PACM is 52.5/eq from literature, and 51.6 g/eq for DFDA. The amine curing agents were mixed with TGEDFDA in stoichiometric amounts and degassed using a THINKY mixer. The samples were cured following the following curing procedure: 60° C. for 2 hours, 80° C. for 2 hours, 160° C. for 3 hours, 180° C. for 1 hour, 200° C. for 1 hour and 220° C. for 1 hour. The following chemical structures are difuran diamine tetra epoxy (TGEDFDA: first), para-bis(amino-cyclohexyl)methane (PACM:second) and difuran diamine (DFDA:third):

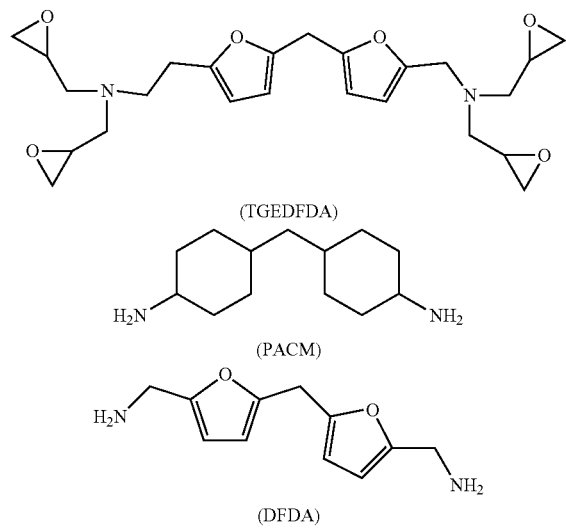

Dynamic Mechanical Properties of the Crosslinked Networks

Dynamic mechanical analysis (DMA, TA Instruments, model Q 800) was used to evaluate the glass transition temperature (Tg), modulus and crosslinking density of the polymer. DMA tests were conducted using single cantilever geometry with a frequency of 1 Hz and amplitude of 10 µm. The temperature ramp rate was 2° C./min. Tg of the system was obtained from the peak of the tan δ curve and the loss storage curve, which are given in the table below, along with room temperature (18° C.) storage modulus and crosslinking density obtained using the rubbery storage modulus values 50° C. above Tg.

TABLE 4

Properties of TGEDFDA cured samples.

| Epoxy/Amine systems | $T_{g, E''}$ (° C.) | $T_{g, tan\delta}$ (° C.) | $E'_{RT}$ (GPa) | V (mol/cc) |
|---|---|---|---|---|
| TGEDFDA/PACM | 143 | 167 | 4.06 | 7.0E−03 |
| TGEDFDA/DFDA | 158 | 205 | 4.53 | 6.1E−03 |

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes, or at least for the purpose described in the context in which the reference was presented.

REFERENCES

The following references may be useful in understanding some of the principles discussed herein:
1. Auvergne, R.; Caillol, S.; David, G.; Boutevin, B.; Pascault, J.-P., Biobased Thermosetting Epoxy: Present and Future. Chemical Reviews 2013, 114 (2), 1082-1115.
2. Baroncini, E. A.; Kumar Yadav, S.; Palmese, G. R.; Stanzione, J. F., Recent advances in bio-based epoxy resins and bio-based epoxy curing agents. Journal of Applied Polymer Science 2016, 133 (45), n/a-n/a.
3. Gandini, A.; Lacerda, T. M.; Carvalho, A. J. F.; Trovatti, E., Progress of Polymers from Renewable Resources: Furans, Vegetable Oils, and Polysaccharides. Chemical Reviews 2016, 116 (3), 1637-1669.
4. Froidevaux, V.; Negrell, C.; Caillol, S.; Pascault, J.-P.; Boutevin, B., Biobased Amines: From Synthesis to Polymers; Present and Future. Chemical Reviews 2016, 116 (22), 14181-14224.
5. Hu, F.; Yadav, S. K.; La Scala, J. J.; Sadler, J. M.; Palmese, G. R., Preparation and Characterization of Fully Furan-Based Renewable Thermosetting Epoxy-Amine Systems. Macromolecular Chemistry and Physics 2015, 216 (13), 1441-1446.

6. Hu, F.; La Scala, J. J.; Sadler, J. M.; Palmese, G. R., Synthesis and Characterization of Thermosetting Furan-Based Epoxy Systems. *Macromolecules* 2014, 47 (10), 3332-3342.
7. Holfinger, M. S.; Conner, A. H.; Holm, D. R.; Hill, C. G., Synthesis of Difurfuryl Diamines by the Acidic Condensation of Furfurylamine with Aldehydes and Their Mechanism of Formation. *The Journal of Organic Chemistry* 1995, 60 (6), 1595-1598.
8. Vanlandingham, M. R.; Eduljee, R. F.; Gillespie, J. W., Moisture diffusion in epoxy systems. *J Appl Polym Sci* 1999, 71 (5), 787-798.
9. van der Wel, G. K.; Adan, O. C. G., Moisture in organic coatings—a review. *Prog Org Coat* 1999, 37 (1-2), 1-14.
10. Crank, J., *The mathematics of diffusion*. Oxford university press: 1979.
11. Kishimoto, A., Diffusion of vapours in organic coatings. *Prog Org Coat* 1972, 1 (2), 91-112.
12. Beaman, R. G.; Morgan, P. W.; Koller, C. R.; Wittbecker, E. L.; Magat, E. E. *J. Polym. Sci.* 1959, 40, 329.
13. Morgan, P. W.; Kwolek, S. L. *J. Polym. Sci.* 1959, 40, 299.
14. Morgan, P. W.; Kwolek, S. L. *J. Polym. Sci.* 1962, 62, 33.
15. Morgan, P. W.; Kwolek, S. L. *J. Polym. Sci., Part A: Polym. Chem.* 1996, 34, 531.
16. Wittbecker, E. L.; Morgan, P. W. *J. Polym. Sci., Part A: Polym. Chem.* 1996, 34, 521.
17. Higashi, F.; Taguchi, Y. *J. Polym. Sci., Polym. Chem. Ed.* 1980, 18, 2875.
18. Higashi, F.; Taguchi, Y. *J. Polym. Sci., Polym. Chem. Ed.* 1981, 19, 3345.
19. Higashi, F.; Taguchi, Y.; Kokubo, N.; Ohta, H. *J. Polym. Sci., Polym. Chem. Ed.* 1981, 19, 2745.

The invention claimed is:
1. A compound selected from:
4-{bis[5-(aminomethyl)furan-2-yl]methyl}-2-methoxyphenol; 4-{bis[5-(aminomethyl)furan-2-yl]methyl}-2,6-dimethoxyphenol;
{[(3,4-dimethoxyphenyl)methanediyl]difuran-5,2-diyl}dimethanamine;
{[(4-methylphenyl)methanediyl]difuran-5,2-diyl}dimethanamine;
({[4-(propan-2-yl)phenyl]methanediyl}difuran-5,2-diyl)dimethanamine;
[(cyclohexylmethanediyl)difuran-5,2-diyl]dimethanamine;
(octane-1,1-diyldifuran-5,2-diyl)dimethanamine;
(dodecane-1,1-diyldifuran-5,2-diyl)dimethanamine; and
(5,5',5'',5'''-(pentane-1,1,5,5-tetrayl)tetrakis(furan-5,2-diyl))tetramethanamine.

* * * * *